(12) United States Patent
Kumar et al.

(10) Patent No.: US 12,350,415 B2
(45) Date of Patent: Jul. 8, 2025

(54) SYSTEMS AND METHODS FOR INLINE FLUID CHARACTERIZATION

(71) Applicant: Stryker Corporation, Portage, MI (US)

(72) Inventors: Mayank Kumar, San Jose, CA (US); Keng-Tsai Lin, San Jose, CA (US); Siddarth Satish, Redwood City, CA (US); Andrew T. Hosford, Idaho Falls, ID (US)

(73) Assignee: Stryker Corporation, Portage, MI (US)

( * ) Notice: Subject to any disclaimer, the term of this patent is extended or adjusted under 35 U.S.C. 154(b) by 1046 days.

(21) Appl. No.: 17/277,991

(22) PCT Filed: Sep. 27, 2019

(86) PCT No.: PCT/US2019/053395
§ 371 (c)(1),
(2) Date: Mar. 19, 2021

(87) PCT Pub. No.: WO2020/069278
PCT Pub. Date: Apr. 2, 2020

(65) Prior Publication Data
US 2022/0008637 A1 Jan. 13, 2022

Related U.S. Application Data

(60) Provisional application No. 62/737,730, filed on Sep. 27, 2018.

(51) Int. Cl.
*A61B 5/026* (2006.01)
*A61B 8/06* (2006.01)
(Continued)

(52) U.S. Cl.
CPC ........... *A61M 1/3609* (2014.02); *A61B 5/026* (2013.01); *A61B 8/06* (2013.01); *G01F 1/663* (2013.01);
(Continued)

(58) Field of Classification Search
CPC . G06T 2207/30104; G06T 7/248; G06T 7/62; G06T 2207/10024; G06T 2207/248;
(Continued)

(56) References Cited

U.S. PATENT DOCUMENTS 4,690,002 A 9/1987 Hubbard et al.
6,954,661 B2 10/2005 Cho et al.
(Continued)

FOREIGN PATENT DOCUMENTS

CN 1573332 A 2/2005
CN 103988057 A 8/2014
(Continued)

OTHER PUBLICATIONS

"International Application Serial No. PCT/US2019/053395, International Preliminary Report on Patentability mailed Oct. 29, 2020", 9 pgs.
(Continued)

*Primary Examiner* — Dionne Pendleton
(74) *Attorney, Agent, or Firm* — Howard & Howard Attorneys PLLC

(57) ABSTRACT

A system performs a method for characterizing passage of a patient fluid through a conduit. The method includes quantifying flow of fluidic content through a conduit, where the fluidic content includes a patient fluid, estimating a concentration of a fluid component of the patient fluid in the fluidic content, and characterizing passage of the patient fluid loss through the conduit based on the quantified flow and the concentration of the fluid component. At least one of the quantified flow or the concentration of the fluid component is based on sensor data from a sensor arrangement coupled to the conduit. Other apparatus and methods are also described.

21 Claims, 13 Drawing Sheets

(51) Int. Cl.
*A61M 1/36* (2006.01)
*G01F 1/663* (2022.01)
*G01F 1/68* (2006.01)
*G01N 33/49* (2006.01)

(52) U.S. Cl.
CPC ............... *G01F 1/68* (2013.01); *G01N 33/49* (2013.01); *A61M 2205/3306* (2013.01); *A61M 2205/3334* (2013.01); *A61M 2205/3375* (2013.01); *A61M 2230/20* (2013.01)

(58) Field of Classification Search
CPC ......... G06T 2207/10016; G06T 7/0016; G06T 2207/30024; G01N 33/49; G01N 2015/1486; G01N 15/01; G01N 15/1434; G01N 15/1468; G01N 15/1484; G01N 2015/1006; G01N 2015/1493; G01N 21/05; G01N 21/25; G01N 33/0004; G01N 33/487; G01N 33/5094; G01N 1/10; G01N 1/30; G01N 15/02005; G01N 15/1012; G01N 15/1433; G01N 15/1456; G01N 15/1459; G01N 2015/0046; G01N 2035/00158; G01N 21/59; G01N 2201/12; G01N 33/491; G01N 33/4915; G01N 33/56972; G01N 33/80; G01F 1/661; G01F 1/663; G01F 1/667; G01F 1/68; G01F 1/6845; G01F 1/7086; G01F 1/712; G01F 15/063; G01F 25/10; G01F 1/00; G01F 1/007; G01F 15/0755; G01F 23/292; G01F 1/6842; G01F 1/6888; G01F 1/696; G01F 15/024; G01F 15/075; G01F 23/2928; A61M 1/3609; A61M 2205/3306; A61M 2205/3334; A61M 2205/3375; A61M 2230/20; A61M 2205/18; A61M 1/3496; A61M 1/38; A61M 16/0051; A61M 16/0465; A61M 16/16; A61M 2016/0039; A61M 2016/1025; A61M 2202/0208; A61M 2202/0415; A61M 2205/331; A61M 2205/3365; A61M 2205/3584; A61M 2205/3592; A61M 2205/502; A61M 2205/702; A61M 2206/14; A61M 2209/0042; A61M 5/14212; A61M 5/063; A61M 1/265; A61M 1/3406; A61M 1/3616; A61M 1/3672; A61M 16/0069; A61M 16/026; A61M 16/0666; A61M 16/1045; A61M 16/107; A61M 16/208; A61M 16/0036; A61M 2202/0007; A61M 2202/0443; A61M 2205/3327; A61M 2205/3553; A61M 2205/50; A61M 2205/75; A61M 2209/00; A61M 2230/005; A61M 2230/42; A61B 5/026; A61B 5/1455; A61B 8/06; A61B 5/6814; A61B 2560/0443; A61B 5/0031; A61B 5/0084; A61B 5/02416; A61B 5/14546; A61B 5/15003; A61B 5/150358; A61B 5/150992; A61B 5/153; A61B 5/411; A61B 5/4851; A61B 5/6843; A61B 5/686; A61B 5/721; A61B 5/7253; A61B 8/10; A61B 8/488; A61B 2505/05; A61B 2560/0214; A61B 2562/00238; A61B 5/0002; A61B 5/002; A61B 5/0059; A61B 5/0075; A61B 5/0816; A61B 5/1126; A61B 5/14535; A61B 5/14551; A61B 5/14552; A61B 5/150213; A61B 5/150221; A61B 5/150229; A61B 5/150755; A61B 5/150862; A61B 5/155; A61B 5/157; A61B 5/6803; A61B 5/6831; A61B 5/6862; A61B 5/6876; A61B 5/7257; A61B 5/726; A61B 8/5261; A41D 20/00; A61F 2/06; A61F 2250/0002; A61F 2/07; A61F 2/2472; B01L 2200/04; B01L 2200/0605; B01L 2200/148; B01L 2200/160883; B01L 2400/0633; B01L 3/502738; B01L 2200/027; B01L 2200/0647; B01L 2200/16; B01L 2300/0627; B01L 2300/0883; B01L 3/502715; B01L 3/502761; Y10T 137/8158; Y02A 20/00; H01J 31/501; G06V 10/764; G06V 20/69; G06V 20/693; G06V 20/698; G06V 2201/03; G06F 18/24; G01P 5/10; G01P 5/12; G01K 13/02; G01K 13/026; G01K 2207/00; G01J 1/4228; G01J 1/44; G01J 3/10; G01J 3/2803; G01J 5/045; G01B 11/026; E03C 1/0408; E03C 2001/0418; E03B 7/04; B05B 1/18; B05B 12/004; B05B 12/008; B05B 12/02; B05B 12/12; A61H 31/004

See application file for complete search history.

(56) References Cited

U.S. PATENT DOCUMENTS

| | | | |
|---|---|---|---|
| 8,347,427 B2 * | 1/2013 | Klicpera | ............... B05B 12/12 4/643 |
| 8,613,226 B2 | 12/2013 | Sugiura et al. | |
| 8,792,693 B2 | 7/2014 | Satish et al. | |
| 8,983,167 B2 | 3/2015 | Satish et al. | |
| 9,773,320 B2 | 9/2017 | Satish et al. | |
| 9,824,441 B2 | 11/2017 | Satish et al. | |
| 10,194,801 B2 | 2/2019 | Elhawary et al. | |
| 10,195,337 B2 | 2/2019 | Koolbergen et al. | |
| 10,285,603 B2 | 5/2019 | Flower | |
| 11,712,183 B2 | 8/2023 | Satish et al. | |
| 2003/0120306 A1 | 6/2003 | Burbank et al. | |
| 2004/0024296 A1 * | 2/2004 | Krotkov | ............... A61B 5/7253 600/322 |
| 2005/0166683 A1 | 8/2005 | Krivitski et al. | |
| 2006/0189926 A1 * | 8/2006 | Hall | ................. A61B 5/150213 600/316 |
| 2007/0299330 A1 | 12/2007 | Couronne et al. | |
| 2011/0009800 A1 * | 1/2011 | Dam | ................... A61M 1/3609 210/90 |
| 2012/0232364 A1 | 9/2012 | Delmage | |
| 2014/0081154 A1 * | 3/2014 | Toth | ..................... A61B 5/0002 600/479 |
| 2014/0214149 A1 | 7/2014 | Kuraguntla et al. | |
| 2015/0254418 A1 | 9/2015 | Sankaran et al. | |
| 2016/0175514 A1 * | 6/2016 | Thill | ..................... G01N 21/25 702/25 |
| 2016/0335779 A1 | 11/2016 | Satish et al. | |
| 2017/0184433 A1 * | 6/2017 | Kostner | ................... G01F 1/696 |
| 2017/0186160 A1 | 6/2017 | Satish et al. | |
| 2017/0290518 A1 | 10/2017 | Akerman et al. | |
| 2018/0110913 A1 * | 4/2018 | Loderer | .................... G01F 1/74 |
| 2018/0160948 A1 * | 6/2018 | Takagi | ................. A61B 5/1455 |
| 2018/0199827 A1 | 7/2018 | Satish et al. | |
| 2020/0260956 A1 * | 8/2020 | Lee | ............ G06F 9/54 |

FOREIGN PATENT DOCUMENTS

| | | |
|---|---|---|
| CN | 104427927 A | 3/2015 |
| CN | 104661582 A | 5/2015 |
| CN | 105658138 A | 6/2016 |
| EP | 1421899 A1 | 5/2004 |
| EP | 1859730 A1 | 11/2007 |
| IN | 2002KOL00581 A1 | 3/2005 |

(56) References Cited

FOREIGN PATENT DOCUMENTS

| JP | H02190767 A | 7/1990 |
|---|---|---|
| JP | 2008501117 A | 1/2008 |
| JP | 2011179940 A | 9/2011 |
| JP | 2016504072 A | 2/2016 |
| JP | 2017508484 A | 3/2017 |
| WO | 2004100788 A1 | 11/2004 |
| WO | 2005119181 A1 | 12/2005 |
| WO | 2013009709 A2 | 1/2013 |
| WO | 2014085395 A1 | 6/2014 |
| WO | WO-2020069278 A1 | 4/2020 |

OTHER PUBLICATIONS

"International Application Serial No. PCT/US2019/053395, International Search Report mailed Dec. 13, 2019", 2 pgs.

"International Application Serial No. PCT/US2019/053395, Written Opinion mailed Dec. 13, 2019", 7 pgs.

"International Application Serial No. PCT/US2019/053395, Response filed Jul. 10, 2020 to Written Opinion mailed Dec. 13, 2019", 4 pgs.

English language abstract and machine-assisted English translation for JPH 02-190767 A extracted from espacenet.com database on Sep. 26, 2023, 6 pages.

"European Application Serial No. 19865915.3, Response to Communication pursuant to Rules 161(2) and 162 EPC filed Nov. 2, 2021", 18 pgs.

English language abstract for CN 104427927 A extracted from espacenet.com database on Apr. 1, 2024, 2 pages.

English language abstract for CN 104661582 A extracted from espacenet.com database on Apr. 1, 2024, 2 pages.

English language abstract for CN 1573332 A extracted from espacenet.com database on Aug. 12, 2024, 2 pages.

English language abstract for CN 103988057 A extracted from espacenet.com database on Aug. 12, 2024, 1 page.

English language abstract for CN 105658138 A extracted from espacenet.com database on Aug. 12, 2024, 1 page.

English language abstract for EP 1 859730 A1 extracted from espacenet.com database on Aug. 12, 2024, 2 pages.

Machine-assisted English translation for IN 2002KOL00581 A1 extracted from Google Translate database on Aug. 20, 2024, 12 pages; see also English language equivalent EP 1 421 899 A1.

English language abstract for JP 2008-501117 A extracted from espacenet.com database on Mar. 24, 2025, 2 pages.

English language abstract for JP 2011-179940 A extracted from espacenet.com database on Mar. 24, 2025, 1 page.

English language abstract for JP 2016-504072 A extracted from espacenet.com database on Mar. 24, 2025, 2 pages.

English language abstract for JP 2017-508484 A extracted from espacenet.com database on Mar. 24, 2025, 2 pages.

* cited by examiner

SYSTEMS AND METHODS FOR INLINE FLUID CHARACTERIZATION

RELATED APPLICATION

This application is a national phase entry of PCT/US2019/053395 filed Sep. 27, 2019, which claims the priority benefit of U.S. Provisional Patent Application No. 62/737,730, filed Sep. 27, 2018 and titled "SYSTEMS AND METHODS FOR IN-LINE FLUID CHARACTERIZATION," which are incorporated herein by reference in their entirety.

TECHNICAL FIELD

The subject matter disclosed herein generally relates to the technical field of special-purpose machines that facilitate characterization of fluid passage, which may include estimation of blood loss or gain, including software-configured computerized variants of such special-purpose machines and improvements to such variants, and to the technologies by which such special-purpose machines become improved.

BACKGROUND

Inaccurate estimation of fluid passage (e.g., fluids lost, fluids processed, or fluids gained) for a patient, such as during a surgical procedure, may put the patient's health at risk on unnecessarily consume medical resources. For example, where the fluid is blood, overestimation of patient blood loss results in the unnecessary consumption of transfusion-grade blood, and may lead to downsides, such as unnecessary clinical risk to the patient and shortages of transfusion-grade blood that may be needed for other patients. As another example, underestimation of patient blood loss may lead to delayed resuscitation and transfusion, increased risk of infections, tissue death, or even patient death, such as in the event of hemorrhage. Similar effects may respectively result from underestimation and overestimation of blood gain (e.g., from a transfusion). Underestimation or overestimation of blood processed (e.g., through a dialysis machine) can unnecessarily prolong such processing or reduce the benefits from such processing.

Furthermore, inaccurate estimation of fluid passage (e.g., fluids lost, fluids processed, or fluids gained) may be a significant contributor to high operating costs and high surgical costs for hospitals, clinics, and other medical facilities. In particular, unnecessary blood transfusions, resultant from overestimation of patient blood loss, lead to higher operating costs for medical institutions. Additionally, delayed blood transfusions, resultant from underestimation of patient blood loss, have been associated with billions of dollars in avoidable patient infections and re-hospitalizations annually. Thus, it may be desirable to have more accurate systems and methods for estimating or otherwise characterizing passage of a patient fluid.

BRIEF DESCRIPTION OF THE DRAWINGS

Some example embodiments are illustrated by way of example and not limitation in the figures of the accompanying drawings.

DETAILED DESCRIPTION

Figure 1:
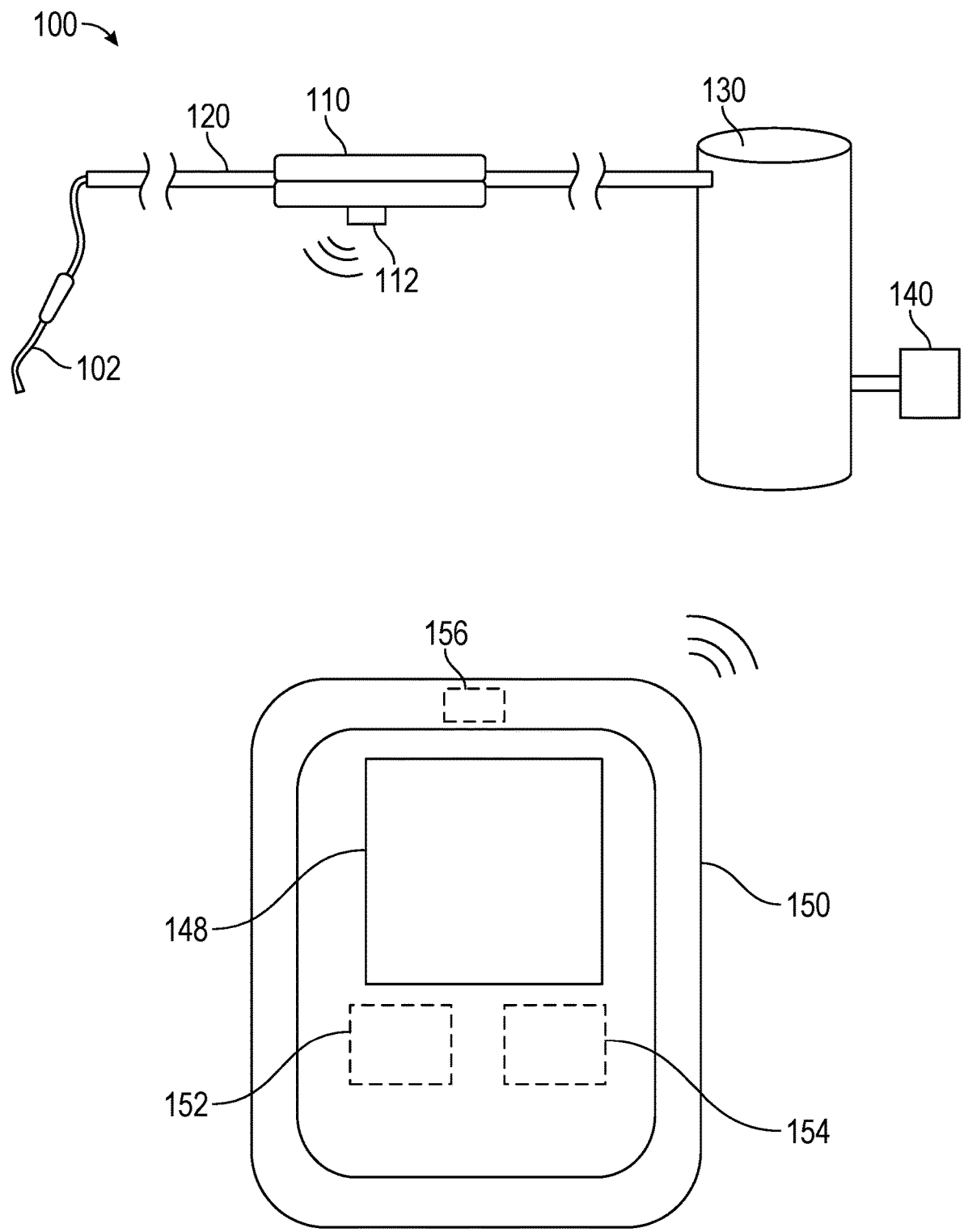
FIG. 1 is a schematic diagram illustrating a system for inline fluid characterization, according to some example embodiments.

Example methods (e.g., procedures or algorithms) facilitate characterizing passage of a fluid that is flowing within a conduit (e.g., fluids from a patient undergoing a medical procedure, which fluids may include blood as a fluid component), and example systems (e.g., special-purpose machines configured by special-purpose software) are configured to facilitate characterizing a fluid flowing within a conduit. Examples merely typify possible variations. Unless explicitly stated otherwise, structures (e.g., structural components, such as modules) are optional and may be combined or subdivided, and operations (e.g., in a procedure, algorithm, or other function) may vary in sequence or be combined or subdivided. In the following description, for purposes of explanation, numerous specific details are set forth to provide a thorough understanding of various example embodiments. It will be evident to one skilled in the art, however, that the present subject matter may be practiced without these specific details.

Generally, an example method for characterizing passage of a patient fluid includes: accessing sensor data from a sensor arrangement coupled to a conduit through which fluidic content is flowing, where the fluidic content includes a patient fluid, quantifying flow of the fluidic content through the conduit, estimating a concentration of a fluid component of the patient fluid in the fluidic content, and characterizing passage of the patient fluid through the conduit based on the quantified flow and the concentration of the fluid component. For example, in some variations, the characterizing of the passage of the patient fluid includes quantifying the volume of the patient fluid flowing through the conduit. The flow rate, the concentration of the fluid component, or both, may be determined (e.g., estimated) based on the sensor data (e.g., sampling data) from the sensor arrangement coupled to the conduit. In some variations, the patient fluid to be characterized is blood, and the fluid component whose concentration is estimated is hemoglobin. In some variations, the method includes reducing the flow of the fluidic content through the conduit while quantifying the flow of the fluidic content, while estimating a concentration of a fluid component of the patient fluid, or both.

There are various suitable ways to quantify flow of fluidic content through a conduit. In some variations, quantifying the flow of fluidic content includes estimating a flow rate of the fluidic content. For example, estimating the flow rate may include using an ultrasound Doppler flow meter to emit ultrasonic waves into the conduit and analyze a frequency shift of ultrasonic waves reflected from the fluidic content. As another example, estimating the flow rate may include using a time-of-flight ultrasound flow meter to emits ultrasonic waves into the conduit and analyze the flight time of ultrasonic waves transmitted through the fluidic content. In another example, estimating the flow rate includes comparing a first optical signal and a second optical signal, where the first optical signal corresponds to light detected at a first location along the conduit and the second optical signal corresponds to light detected at a second location along the conduit. Comparison of the first and second optical signals may be used to estimate the flow rate of the fluidic content in the conduit. In some variations, quantifying flow of fluidic content includes estimating a thermal mass flow of the fluidic content. For example, estimating a thermal mass flow of the fluidic content may include introducing a known amount of heat into a flow of fluidic content and measuring the associated temperature change (e.g., maintaining a probe at a constant temperature within the fluidic content and measuring the energy consumed in doing so). As another example, estimating a thermal mass flow of the fluidic content may include introducing a known amount of heat into the flow of fluidic content and measuring the change in temperature of the fluidic content at some point downstream.

Furthermore, there are various suitable ways to estimate the concentration of a fluid component in the fluidic content. For example, estimating the concentration of a fluid component may include analyzing a multispectral image of the conduit. As another example, estimating the concentration of a fluid component may include applying a machine learning algorithm to a color image of the conduit. Furthermore, in some variations, the method may include performing a spectroscopy analysis to determine composition of the fluidic content.

Generally, an example system for characterizing passage of patient fluid through a conduit includes a conduit configured to convey fluidic content that includes a patient fluid, a sensor arrangement couplable to the conduit, where the sensor arrangement includes at least one sensor configured to generate sensor data based on the fluidic content, and one or more processors configured to perform operations that include accessing the sensor data, quantifying flow of the fluidic content through the conduit, estimating a concentration of a fluid component of the patient fluid in the fluidic content, and characterizing passage of the patient fluid through the conduit based on the quantified flow and the concentration of the fluid component.

The sensor arrangement may include any suitable form factor configured for coupling to the conduit. For example, in some variations, the sensor arrangement may include a housing configured to cover at least a portion of the conduit, and may be configured to clamp onto or slide over the conduit. For example, the housing can include jaws configured to clamp onto the conduit. As another example, the system may further include a conduit insert that is couplable inline with the conduit.

The sensor arrangement may include any combination of one or more suitable sensors for quantifying a flow, determining a concentration of a fluid component, or both. For example, the sensor arrangement may include an ultrasound flow rate sensor, a thermal mass flow sensor, or any suitable combination thereof. In some variations, the sensor arrangement includes at least one optical sensor configured to detect light transmitted through the fluidic content. For example, the sensor arrangement may include a plurality of optical sensors arranged at a plurality of axial locations along the conduit, at a plurality of circumferential locations around the conduit, or any suitable combination thereof. In some variations, the sensor arrangement includes one or more optical sensors, thermal sensors, ultrasound sensors, or any suitable combination thereof. Furthermore, such sensors may include one or more optical sensor arrays configured to perform multispectral or spectroscopic imaging, color imaging, or both, to facilitate estimating a concentration of a fluid component.

In some example embodiments, a system includes:
   a conduit configured to convey fluidic content that includes a patient fluid;
   a sensor arrangement coupled to the conduit and including at least one sensor configured to generate sensor data based on the fluidic content; and
   one or more processors configured to perform operations comprising:

accessing the sensor data from the sensor arrangement coupled to the conduit through which the fluidic content is flowing, the fluidic content including the patient fluid;

quantifying flow of the fluidic content flowing through the conduit;

estimating a concentration of a fluid component of the patient fluid in the fluidic content flowing through the conduit; and characterizing passage of the patient fluid through the conduit based on the quantified flow of the fluidic content and on the estimated concentration of the fluid component in the fluidic content, at least one of the quantifying of the flow or the estimating of the concentration being based on the sensor data from the sensor arrangement coupled to the conduit.

In certain example embodiments, a method includes:

accessing sensor data from a sensor arrangement coupled to a conduit through which fluidic content is flowing, the fluidic content including a patient fluid;

quantifying flow of the fluidic content flowing through the conduit;

estimating a concentration of a fluid component of the patient fluid in the fluidic content flowing through the conduit; and by one or more processors, characterizing passage of the patient fluid through the conduit based on the quantified flow of the fluidic content and on the estimated concentration of the fluid component in the fluidic content, at least one of the quantifying of the flow or the estimating of the concentration being based on the sensor data from the sensor arrangement coupled to the conduit.

In various example embodiments, a machine-readable medium includes instructions that, when executed by one or more processors of a machine, cause the machine to perform operations including:

accessing sensor data from a sensor arrangement coupled to a conduit through which fluidic content is flowing, the fluidic content including a patient fluid;

quantifying flow of the fluidic content flowing through the conduit;

estimating a concentration of a fluid component in the fluidic content flowing through the conduit; and characterizing passage of the patient fluid through the conduit based on the quantified flow of the fluidic content and on the estimated concentration of the fluid component in the fluidic content, at least one of the quantifying of the flow or the estimating of the concentration being based on the sensor data from the sensor arrangement coupled to the conduit.

Generally, the methods and systems discussed herein are operable to characterize passage of a patient fluid flowing through a conduit (e.g., among other fluidic content). Such passage of the patient fluid includes loss of the patient fluid by the patient (e.g., where the conduit conveys collected blood that was lost during surgery), gain of the patient fluid by the patient (e.g., where the conduit conveys blood being transfused into the patient), processing of the patient fluid (e.g., where the conduit conveys blood being processed through a dialysis machine), or any suitable combination thereof. For clarity and brevity, many illustrative examples discussed herein focus on situations where the patient fluid (e.g., blood) is lost by the patient. However, the methods and systems discussed herein are generally applicable to characterizing any passage of any patient fluid (e.g., urine or amniotic fluid), including passage into the patient, passage out of the patient, both (e.g., in processing the patient fluid), or neither (e.g., passage from one container to another container).

For example, the methods and systems described herein may be used to characterize fluids (e.g., bodily fluids) that are lost by a patient during a medical procedure (e.g., labor and delivery, surgical procedure, etc.). For example, the methods and systems may be used to track or otherwise estimate a quantity of fluid component (e.g., blood) lost by a patient throughout a medical procedure, and the estimate may be updated and displayed in substantially real-time during the procedure, at the conclusion of the procedure, or both. These methods and systems may be used in a variety of settings, including in a hospital or clinic setting (e.g., an operating room), a military setting (e.g., a battlefield), or other suitable medical treatment settings. This information can be used to improve medical treatment of patients. For example, medical practitioners (e.g., nurses or surgeons) who receive this information during a surgical procedure, after the surgical procedure, or both, can then make appropriate decisions for treatment of the patient (e.g., determining whether to provide a blood transfusion to the patient and how much blood to transfuse) based on the improved accuracy of this information on patient status. For example, armed with more accurate information on the patient fluid loss or patient status, medical practitioners can better avoid delayed blood transfusions, thereby improving patient outcomes. Additionally, medical practitioners can avoid providing unnecessary blood transfusions, which unnecessarily deplete inventories of transfusable blood, increase operating costs and medical bills, and increase health risks for the patient.

Estimates of the quantity of patient fluid collected may be aggregated into a running total or an overall estimate of the quantity of patient fluid lost by the patient during the procedure. Such estimates may, in some example embodiments, be combined with estimates of fluid collected in batches, fluid collected cumulatively over time, or both. For example, a total volume of fluid, a total rate of patient fluid loss, or both, may be estimated at any particular point during the procedure, after the procedure, or both.

In some variations, for a patient fluid of interest (e.g., blood), estimated quantities of the patient fluid from multiple sources are aggregated to generate an estimate of total loss of the patient fluid. For example, extracorporeal fluids lost by the patient may be collected in a container, such as a canister or other fluid receptacle (e.g., collected with a suction wand, as described below). Additionally or alternatively, fluid lost by the patient may be collected with surgical textiles or other absorbent items, such as surgical sponges (e.g., laparotomy sponges), surgical dressings, surgical gauze, surgical towels, absorbent pads (e.g., chux pads), absorbent drapes, vaginal packs, other textiles, other absorbent items, or any suitable combination thereof. Textiles or absorbent items may be placed in a bag (e.g., sponge count bag) for tracking purposes, hygienic purposes, etc. Furthermore, collection of lost fluids may be performed with a specialized container. For example, during labor and delivery procedures, a drape with at least one pocket (e.g., a blood collection V-drape with a triangular pocket) may be placed under the patient for collecting blood, amniotic fluid, urine, etc. In some variations, the quantity of fluid collected in an item, such as a surgical textile or a canister, is estimated based on a measured weight (e.g., indicating mass) of the item when containing fluid. In some variations, the quantity of fluid collected in an item, such as a surgical textile or a canisters, is estimated using one or more of the methods or systems described in U.S. Pat. Nos. 8,792,693, 8,983,167, 9,824,441, 9,773,320, U.S. Patent Publication No. 2016/0335779, U.S. Patent Publication No. 2017/0186160, U.S. Patent Publication No. 2018/01 99827, each of which is herein incorporated by reference in its entirety.

The system and methods described herein, by way of example, for inline fluid characterization facilitate characterization of fluidic content within a conduit. For example, during a medical procedure, patient fluids may be collected in a receptacle, passed into a conduit, and then directed into another receptacle, such as a sealed waste management system. As shown in FIG. 1, a fluid retrieval device 102 (e.g., a suction wand) or other source of patient fluids collects patient fluids from a surgical site, a canister, a surgical textile, or other fluid source containing fluids to be characterized or otherwise assessed. The collected patient fluids may be passed via tubing into a conduit 120 and may continue to flow into a receptacle 130 (e.g., a canister or a sealed waste management system). In other words, the conduit 120 may be placed in fluidic communication with the fluid retrieval device 102 (or other fluid source) and the receptacle 130. In some variations, the conduit 120, the fluid retrieval device 102, or both, may be in fluidic communication with a vacuum source 140 (e.g., a vacuum pump of the receptacle 130) configured to provide suction to the fluid retrieval device 102 for collecting fluids.

In some variations, the inline fluid characterization systems described herein can be integrated into preexisting setups with waste management systems that collect patient fluids, without extensive equipment additions or modifications. For example, as shown generally in FIG. 1, a system 100 for characterizing patient fluid loss by a patient includes a sensor arrangement 110 couplable to the conduit 120. The sensor arrangement 110 enables inline fluid characterization and includes one or more sensors or other measurement devices (e.g., using various measurement modalities) for characterizing one or more properties of the fluid within the conduit 120. Various kinds of sensors that may be included in the sensor arrangement 110 are described in further detail below. The system 100 may further include at least one processor configured to characterize patient fluid loss based at least in part on the sensor data, as further described below. Sensor data, results of analyzing the sensor data, or both, may be communicated by, for example, a transmission system 112 (e.g., wireless transmission system) to any suitable external device, as further described below.

Unlike the systems and methods discussed herein, various existing systems for analyzing fluid component concentrations in a conduit rely upon a pre-defined set of conditions to perform their analysis. For example, simplified flow conditions, such as laminar flow at a constant or controlled volumetric flow rate may be constrain some existing systems. In contrast, the methods and systems described herein analyze a range of types of flow in the conduit, including laminar flow, turbulent flow, flow at varying velocity or flow rate, intermittent flow, and flow of mixed fluidic content (e.g., a mixture of patient blood, patient urine, saline, and air), all of which may occur in unpredictable fashion when fluids are collected through a fluid retrieval device (e.g., the fluid retrieval device 102) during a medical procedure. Furthermore, some variants of the methods and systems described herein isolate parameters of interest for a selected fluid component of the fluidic content in the conduit. The inline fluid characterization methods and systems can, for example, quantify specifically a patient fluid loss (e.g., blood loss) while the patient fluid is collected and passes through a conduit (e.g., the conduit 120), even under unpredictable flow conditions and while mixed with other fluids such as saline and air.

Example Sensor Arrangement

Generally, as shown in FIG. 1, the system 100 includes the sensor arrangement 110, which is configured to couple to the conduit 120 for enabling inline characterization of fluidic content in the conduit 120. The sensor arrangement 110 includes at least one sensor, which may be configured to quantify a flow of fluidic content through the conduit, estimate a concentration of a fluid component in the patient fluid, or both. The fluidic content includes at least one patient fluid (e.g., blood or urine), possibly one or more other fluids (e.g., saline or air), or a combination thereof. The sensor arrangement may be at least partially disposed within a housing that supports the sensor components (e.g., one or more sensors, corresponding sensor electronics, a data transmitter, a processor, etc.).

Sensor data may be stored locally, analyzed locally, or both, by one or more processors located in or near the sensor arrangement 110. As shown in FIG. 1, the sensor data may be transmitted via a transmission system 112 (e.g., a wireless or wired transmitter) configured to communicate with a computing device 150 (e.g., a remote computing device) for analysis. Examples of the computing device 150 are further described below with respect to FIG. 18. For example, patient fluid loss may be characterized based at least in part on quantified flow of patient fluid in the conduit 120 and the concentration of a fluid component (e.g., blood) in the patient fluid, as further described below.

Example Housing

The sensor arrangement 110 may be at least partially disposed in a housing that supports at least some components of the sensor arrangement 110 and its accompanying electronics. The housing may also couple the sensor arrangement 110 to the conduit 120, one or more other conduits or conduit branches, or any suitable combination thereof. Alternatively, at least some of the sensors and other components of the sensor arrangement 110 may be separately coupled to the conduit 120 (e.g., outside of a single common housing), such as being individually coupled to the conduit 120. Accordingly, in some variations, the sensor arrangement 110 may be adjustable or universal in the sense that, for example, the housing, the individual components, or any suitable combination thereof (e.g., one or more groups of grouped components), can be coupled to a wide range of conduit types (e.g., without reliance on being coupled to any specific type or brand of conduit).

Figure 2A:
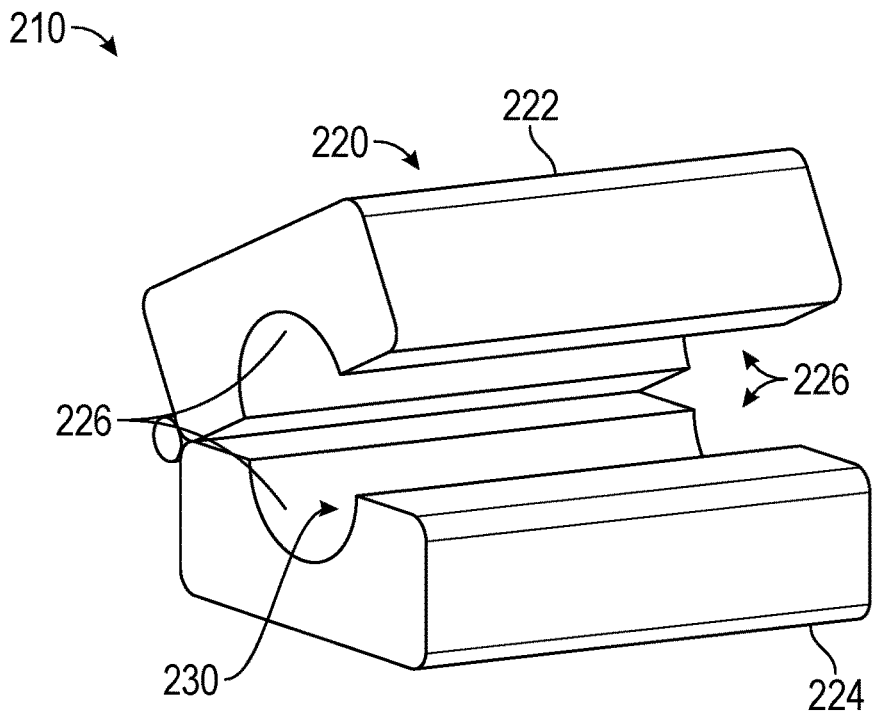
FIG. 2A is a perspective view of a housing for a sensor arrangement, according to some example embodiments.

In some variations, the housing is configured to clamp onto the conduit 120. For example, as shown in FIG. 2A, a housing 220 for a sensor arrangement 210 may include at least a first jaw 222 and a second jaw 224, which together are configured to clamp onto the conduit 120. Each jaw 222 or 224 may, for example, include at least one conduit seat 226 shaped and sized to receive a segment of the conduit 120, which is shown as a conduit 250 in FIGS. 2B and 2C. For example, to receive a conduit (e.g., the conduit 250) having a circular cross-section, each jaw 222 or 224 may include a semicircular conduit seat (e.g., conduit seat 226). The conduit seat 226 may be configured (e.g., shaped) to position the conduit 250 relative to one or more sensors 230 and other components within the sensor arrangement 210. As shown in FIG. 2A, one or more conduit seats 226 may be defined by cutouts on side walls of one or both jaws 222 and 224. Alternatively, each conduit seat 226 can include an elongated, semi-circular recessed surface that extends along the length of the housing 220 such that, when the housing 220 clamps onto the conduit 250, the conduit seats 226 collectively form a lumen extending along the length of the housing. Sensors (e.g., sensor arrangements as described in further detail below) may be disposed along such conduit seat surfaces.

Figures 2B, 2C:
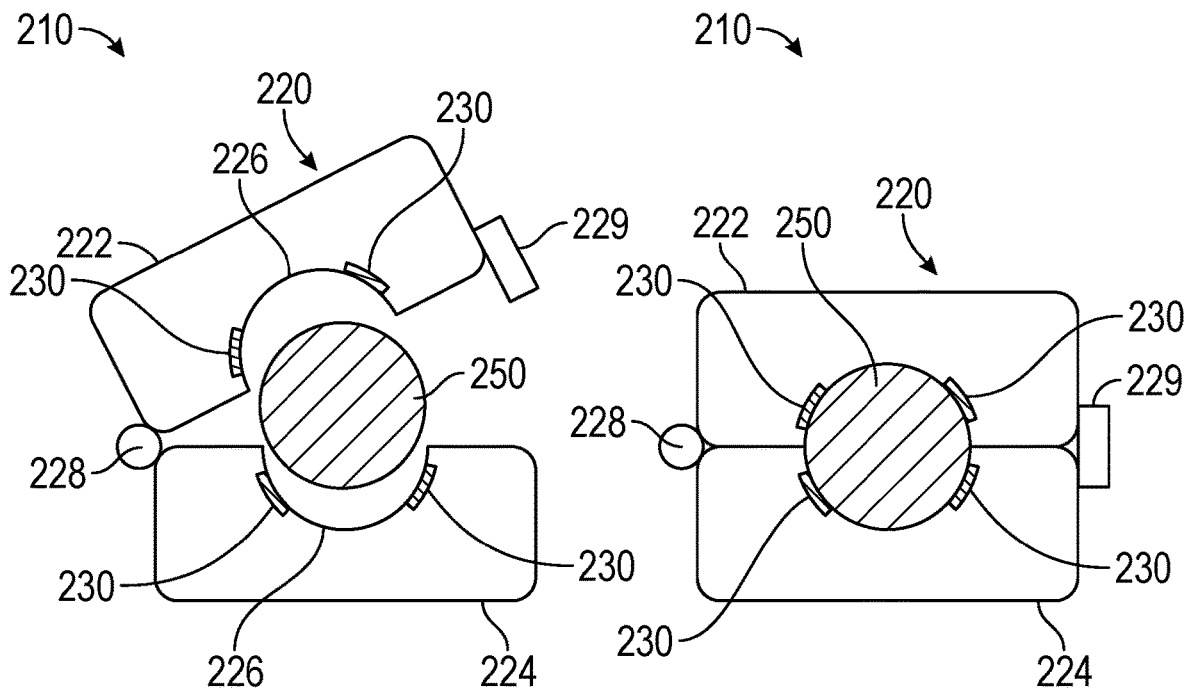
FIGS. 2B and 2C are cross-sectional views of the housing depicted in FIG. 2A, according to some example embodiments.

As shown in the cross-sectional views of FIGS. 2B and 2C, first and second jaws 222 and 224 may be coupled by at least one joint 228 that enables the housing to open (FIG. 2B) and close (FIG. 2C) around a conduit (e.g., the conduit 250). The joint 228 may include, for example, a hinge or other pin joint. The jaws 222 and 224 may include one joint (e.g., the joint 228) extending along the length of the housing 220 or multiple such joints distributed along the length of the housing 220. In some variations, the joint 228 may be spring-loaded, such as with a torsional spring, to be biased closed or biased open. Additionally or alternatively, the joint 228 may include one or more detents that bias the jaws to be positioned at any angle among a predetermined, discrete set of angles. Although FIGS. 2B and 2C illustrate the first and second jaws 222 and 224 to be substantially identical or symmetrical (e.g., each forming half of the housing 220), it should be understood that the housing 220 may include jaws of any suitable sizes relative to each other (e.g., a deeper main jaw coupled to a shallower lid-like jaw). Furthermore, the housing 220 may include three, four, or other suitable numbers of jaws. In other variations, the housing 220 may be configured to wrap around the conduit 250 (e.g., with a C-shaped cross-section that engages the conduit 250 laterally).

The housing 220 may further include one or more securing elements 229 configured for securing the housing 220 in a closed position. A securement element 229 may include, for example, a latch, mating snap feature, magnet, etc. In some variations, the housing 220 may include one or more sealing elements (e.g., around the conduit seats 226, around the interface between the jaws 222 and 224, etc.), such as a gasket material, to fully enclose a segment of the conduit 250 within the housing 220, in a substantially liquid-tight manner, air-tight manner, or both. Furthermore, in some variations, the housing 220, the sealing elements, or both, may be opaque (e.g., made of opaque material) to help prevent ambient light from entering the housing 220, since such ambient light may interfere with sensor readings within the housing 220.

The housing 220 may be sized to couple to a conduit (e.g., the conduit 250) that has a predetermined diameter. For example, the housing 220 may be configured to receive or otherwise couple to a conduit having a diameter between about 4 mm and about 20 mm, or any suitable size conduit. In other variations, the housing 220 may be adjustable to securely couple to conduits with a variety of diameters. For example, to accommodate a range of conduit diameters without resulting in a loose coupling around the conduit, one or more of the conduit seats 226 may include a deformable surface that can compress, such that the housing 220 can receive and conform to larger conduit diameters, increase in volume to receive and conform to smaller conduit diameters, or both. For example, the deformable surface can include padding, other deformable material, an inflatable surface, etc. In some variations, the conduit seats 226 may be adjustable in size, such as with a mechanism similar to a leaf shutter.

Figure 3A:
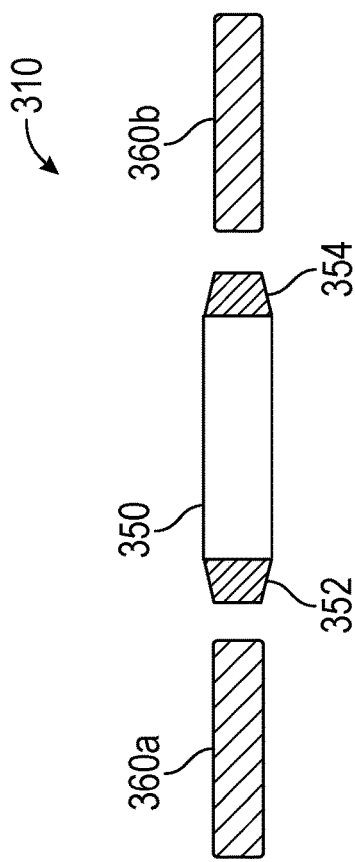
FIG. 3A is a schematic diagram illustrating a conduit segment insert, according to some example embodiments.
Figure 3B:
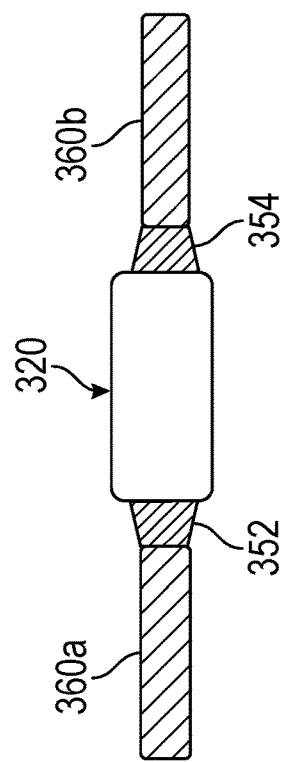
FIG. 3B is a schematic diagram illustrating a sensor arrangement coupled to the conduit segment insert depicted in FIG. 3A, according to some example embodiments.

FIGS. 3A and 3B illustrate another variation of a sensor arrangement 310 with a conduit segment (e.g., a reusable or disposable conduit insert) that is couplable to one or more other conduit segments. As shown in FIG. 3A, the system 100 may include a conduit segment 350 that may be inserted inline between other conduit portions 360a and 360b. The conduit segment 350 may include an inner volume that can be placed in fluidic communication with the conduit portion 360a at an inlet end, and in fluidic communication with the conduit portion 360b at an outlet end. For example, the conduit segment 350 may be coupled inline with other conduit portions 360a and 360b via connectors 352 and 354, which may be, for example, tubing sleeve connectors, threaded connectors, or any suitable connectors. As shown in FIG. 3B, a housing 320 with sensors may be placed over the conduit segment 350. The housing 320 may include a lumen or other conduit receiving surface. For example, the housing 320 may include a plurality of jaws (e.g., similar to the jaws 222 and 224 described above with respect to FIGS. 2A-2C) or have a C-shaped cross section that wraps around the conduit segment 350. In some variations, the conduit segment 350 is disposable and intended for single use, while the housing 320 is reusable. However, in other variations, the conduit segment 350 may be designed for multiple reuses, the housing 320 may disposable after a single use or limited number of uses, or any suitable combination thereof.

Figure 4A:
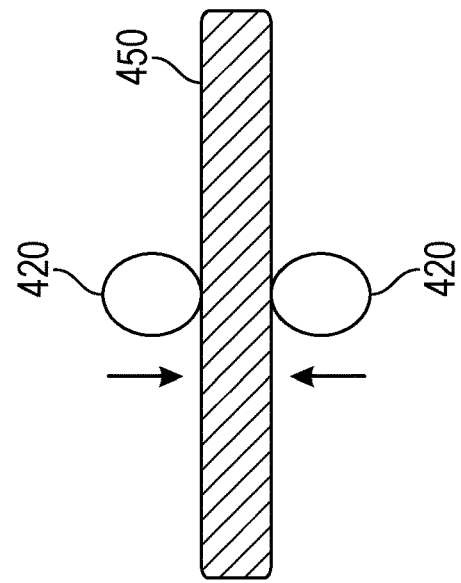
FIG. 4A is a schematic diagram illustrating a pinching mechanism for a conduit, according to some example embodiments.
Figure 4B:
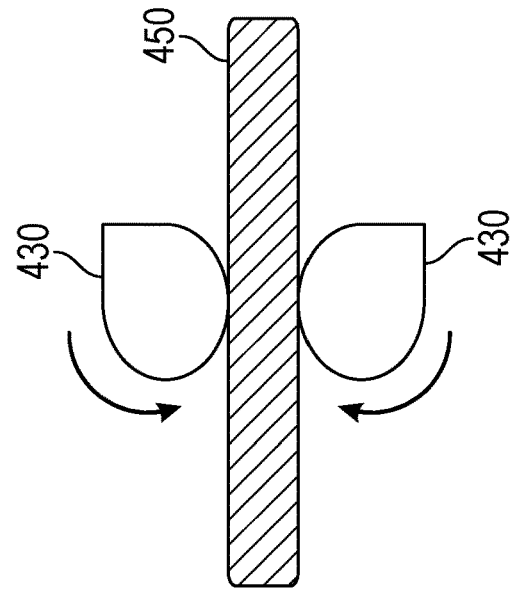
FIG. 4B is a schematic diagram illustrating another pinching mechanism for a conduit, according to some example embodiments.
Figure 5:
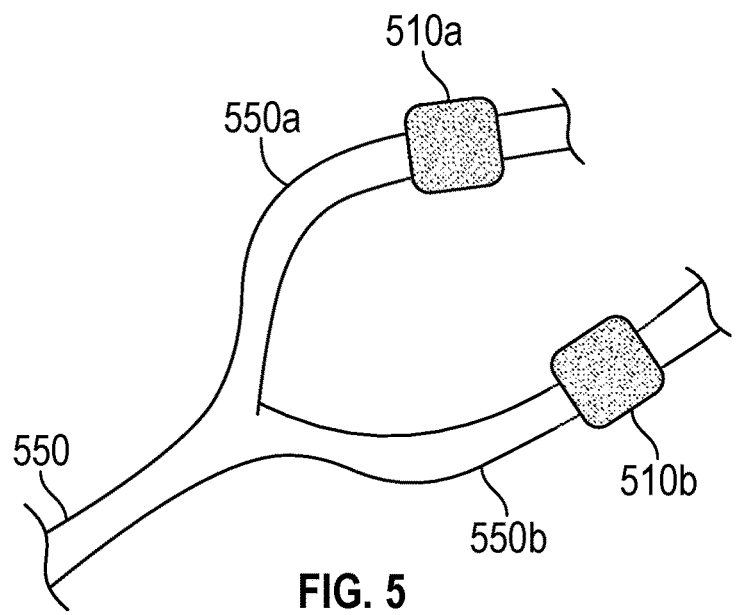
FIG. 5 is schematic diagram illustrating a branched conduit with alternating pinching mechanisms, according to some example embodiments.

In some variations, the housing 320 includes a pinch mechanism to temporarily reduce flow (e.g., pause or temporarily slow the flow) of the fluidic content through the fully or partially enclosed conduit (e.g., the conduit segment 350), so as to momentarily achieve a somewhat stable state of flow for sensor measurement to occur. The pinch mechanism may be configured to fully or partially close off the conduit at one or more axial locations along the conduit. For example, as shown in FIG. 4A, the pinch mechanism may include pincher elements 420 that are opposed across a conduit 450 and may be actuated to move toward each other to reduce or stop flow through the conduit 450. As another example, as shown in FIG. 4B, the pinch mechanism may include cams 430, at least one having a varying radius, such that rotation of the cams 430 causes the cams 430 to reduce or stop flow through the conduit 450. In some variants, the reduction or stoppage of the flow is cyclical (e.g., periodic) with continuous rotation of the cams 430. Alternatively, the pinch mechanism may include only one pincher element 420 or only one cam 430 that is opposed a static surface (e.g., planar surface). The housing may, in some variations, include two or more pinch mechanisms. For example, as shown in FIG. 5, a conduit 550 may be bifurcated into two conduit branches 550a and 55b (e.g., later reunited downstream), and two pinch mechanisms 510a and 510b may be respectively coupled to the conduit branches 550a and 550b. When one pinch mechanism is actuated to reduce flow in its corresponding conduit branch, a set of sensors located upstream of the pinch mechanism may perform measurements. By actuating the pinch mechanisms 510a and 510b in an alternating manner, the system 100 may perform measurements of fluidic content in the conduit 550 without substantially restricting overall volumetric flow or substantially hampering upstream suction of patient fluids. In some variations, the division of a conduit (e.g., the conduit 550) into two or more conduit branches may be accomplished with a conduit segment, such as the inserted conduit segment 350 described above. Any of the above-described arrangements may be substantially contained in the housing.

Other variations of the housing may couple to the conduit in any suitable manner. For example, in addition to clamping onto the conduit (e.g., the conduit 120, 250, 450, or 550) as described above, the housing may be configured to slide over the conduit like a sleeve, or wrap around the conduit (e.g., in a spiral). Furthermore, as described above, in some variations, a disposable conduit segment and a reusable housing unit can be coupled together and inserted inline with other conduit portions.

Example Sensors

The sensor arrangement (e.g., the sensor arrangement 110, 210, or 310) may include one or more sensors configured to quantify a flow (e.g., estimate a velocity of the flow, a mass flow rate of the flow, a volume flow rate of the flow, or any suitable combination thereof), estimate a fluid component concentration, or both. Generally, the one or more sensors may be positioned on or near an external surface of the conduit (e.g., the conduit 120, 250, 450, or 550). In some variations, as described below, a sensor may be configured to quantify a velocity of the flow though the conduit. In other variations, as described below, a sensor may be configured to quantify mass of fluidic content flowing through the conduit. Furthermore, volumetric measurements of the fluidic content may be derived from the quantified flow measurements. For example, the volumetric flow rate through the conduit may be derived from the flow rate (e.g., flow velocity). In situations where the entire profile of the conduit is filled with fluidic content, then the volumetric flow rate is the quantified flow velocity multiplied by the cross-sectional area of the conduit. As another example, the volume of fluidic content flowing through the conduit may be determined from the measured mass of the fluidic content. In situations where the fluidic content is uniform, the fluidic content volume is the quantified mass of the fluidic content divided by a known density of the fluidic content. Other volumetric measurements may be derived based on the quantified flow and other information relating to the composition of the fluidic content (e.g., through spectroscopic analysis, as described in further detail below). In some variations, one or more volumetric measurements are used to specifically quantify patient fluid passing through the conduit, which may in turn be used to help quantify overall patient fluid loss.

Example Ultrasound Flow Sensors

Figure 6A:
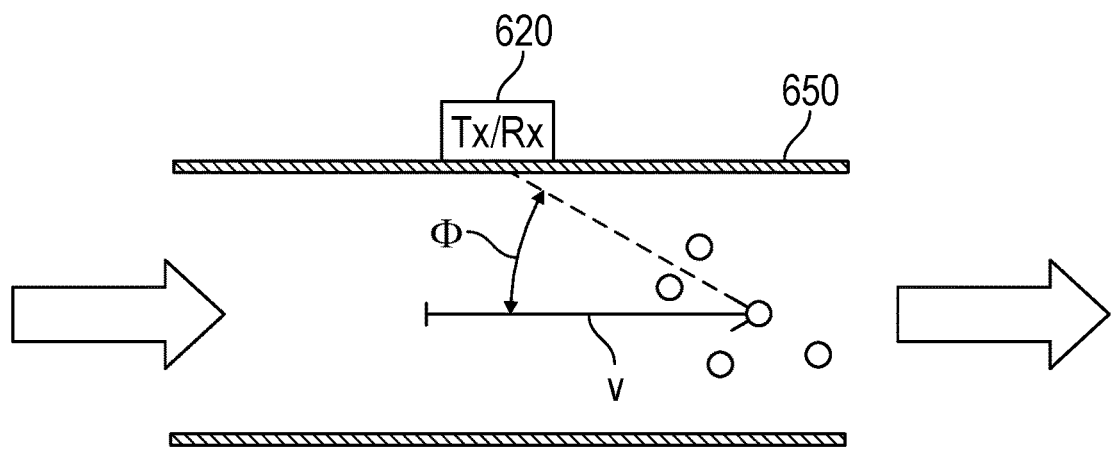
FIG. 6A is a schematic diagram illustrating an ultrasound flow sensor, according to some example embodiments.

In some variations, the sensor arrangement (e.g., the sensor arrangement 110, 210, or 310) includes one or more ultrasound flow sensors. For example, as shown in FIG. 6A, the sensor arrangement may include at least one ultrasound Doppler flow meter 620 that is located adjacent or proximate a conduit 650 in which fluidic content is flowing. The ultrasound Doppler meter 620 may include transducer including a transmitter (Tx) configured to emit a beam of ultrasonic waves into the conduit 650 and a receiver (Rx) configured to detect ultrasonic waves that are reflected by the fluidic content in the conduit 650. The frequency shift of the reflected ultrasonic waves may be analyzed to determine relative motion among the transmitter, the fluidic content, and the receiver. With the transmitter and receiver fixed relative to the conduit 650, the measured relative motion may be correlated to flow rate of the fluidic content in the conduit 650.

Generally, flow rate can be estimated based on Equation 1 below:

$$V = c \frac{f_r - f_t}{2 f_t \cos(\Phi)} \quad (1)$$

where V=flow rate, c=speed of sound in the fluidic content, $f_t$=transmitted frequency, $f_r$=received frequency, and $\Phi$=relative angle between the transmitted ultrasonic beam and the fluid flow direction. Some of these parameters, such as speed of sound in the fluidic content, depends on the composition (e.g., fluid components) of the fluidic content in the conduit 650. Accordingly, in some variations, varying values of c for speed of sound may be used in Equation 1. For example, the composition of the fluidic content in the conduit 650 may be determined separately (e.g., through spectroscopic analysis, as described below) such that relative amounts of various fluid components (e.g., blood, saline, air, etc.) are determined. A representative value of c for use in Equation 1 may be generated based on the composition of the fluidic content. For example, the representative value of c may be a weighted average of c for the various fluid components in the conduit 650. As another example, the representative value of c may be determined based on a look-up table of speeds of speed for different types of fluid, different compositions (e.g., mixtures) of various fluid components, or any suitable combination thereof. In other variations, a fixed representative value of c (e.g., an average value of speeds of sound for all expected fluidic components of the fluidic content) may be used in Equation 1.

Figure 6B:
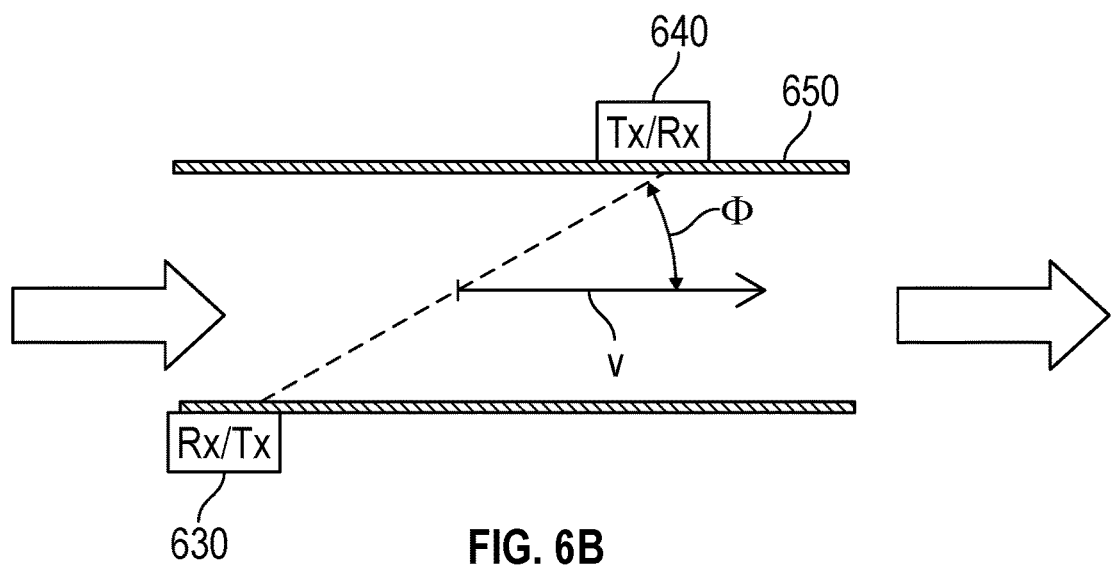
FIG. 6B is a schematic diagram illustrating another ultrasound flow sensor, according to some example embodiments.

In another variation, as shown in FIG. 6B, the sensor arrangement (e.g., the sensor arrangement 110, 210, or 310) includes one or more time-of-flight (ToF) ultrasound flow meters. For example, a ToF flow meter may include two transducers, including an upstream transducer 630 and a downstream transducer 640 located on opposite sides of the conduit 650. The upstream transducer 630 may include a transmitter configured to emit a beam of ultrasonic waves toward a receiver in the downstream transducer 640 (e.g., generally in the direction of flow). Conversely, the downstream transducer 640 may include a transmitter configured to emit a second beam of ultrasonic waves toward a receiver in the upstream transducer 630 (e.g., generally against the direction of flow). In other variations, the upstream and downstream transducers are located on the same side of the conduit 650 but direct ultrasound waves toward an acoustically reflective (e.g., acousto-reflective) surface on the opposite side of the conduit 650. The difference in travel times of the ultrasonic waves propagating with and against the direction of flow may be analyzed to determine the flow rate of the fluidic content in the conduit 650.

Generally, flow rate along the sound path of the ultrasonic beams (which may be an approximation for flow rate in the flow direction) can be estimated based on Equation 2 below:

$$V = \frac{L}{2\cos(\Phi)} \frac{t_{up} - t_{down}}{t_{up} t_{down}} \quad (2)$$

where V=flow rate, L=distance between the upstream and downstream transducers, $t_{up}$=transit time in upstream direction, $t_{down}$=transit time in downstream direction, and $\Phi$=relative angle between the transmitted ultrasonic beams and the fluid flow direction.

In some variations, the sensor arrangement (e.g., the sensor arrangement 110, 210, or 310) includes multiple kinds of ultrasound flow meters. For example, the sensor arrangement may include at least one ultrasound Doppler flow meter (e.g., similar to the flow meter described above with respect to FIG. 6A) and at least one ToF flow meter (e.g., similar to the flow meter described above with respect to FIG. 6B). The combination of both kinds of ultrasound flow meters may, for example, expand the range of conditions under which flow rate can be measured. Generally, an ultrasound Doppler flow meter can detect and analyze ultrasound waves that reflect off particles or other distinct features in the fluidic content flowing in the conduit 650 (e.g., blood cells, air bubbles, overall turbulence of the fluid itself, or any suitable combination thereof). Under certain conditions (e.g., pure laminar flow of saline that lacks particles), the ultrasound Doppler flow meter may provide less accurate measurements. On the other hand, a ToF flow meter can detect and analyze transmitted ultrasound waves in laminar flow without particles. Accordingly, the combination of a Doppler flow meter and a ToF flow meter may enable accurate flow rate measurements under a wider range of operating conditions, including both turbulent and laminar flow, and flow of fluids with and without particles.

Example Optical Flow Sensors

Figure 7A:
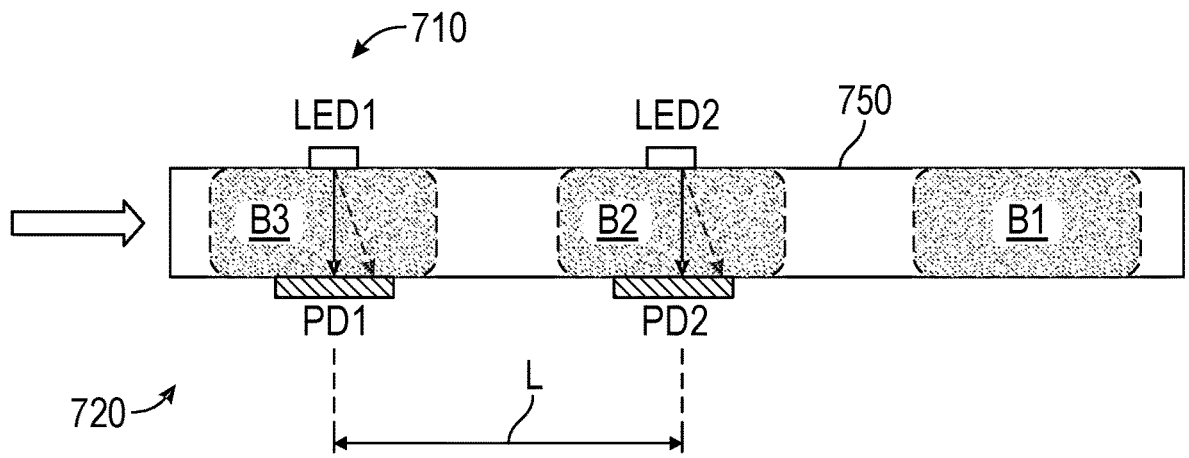
FIG. 7A is schematic diagram illustrating an optical flow sensor, according to some example embodiments.

In yet other variations, the sensor arrangement (e.g., the sensor arrangement 110, 210, or 310) includes one or more optical sensors configured to measure flow rate of the fluidic content in the conduit (e.g., the conduit 120, 250, 450, 550, or 650). For example, as shown in FIG. 7A, the sensor arrangement may include an emitter array 710 and a detector array 720 located generally on opposite sides of a conduit 750. The emitter array 710 may include a series of optical emitters (e.g., LEDs), and the detector array 720 may include a series of optical detectors (e.g., CMOS sensors), with opposing optical emitters and optical detectors forming a series of emitter-detector pairs. Each optical emitter is configured to emit light toward its corresponding optical detector, such that the emitted light is transmitted through the fluidic content in the conduit 750. In some variations, at least some optical emitters may be configured to emit a predetermined wavelength of light based on absorption characteristics of a substance of interest (e.g., blood or hemoglobin). For example, at least some optical emitters may be configured to emit light having a wavelength of around 532 nm, such that the emitted light is optimized for maximal absorption by hemoglobin in the fluidic content in the conduit 750. Additionally or alternatively, in some variations, at least some optical emitters may be configured to emit a broad range of wavelengths (e.g., white light having a broad spectrum).

Figure 7B:
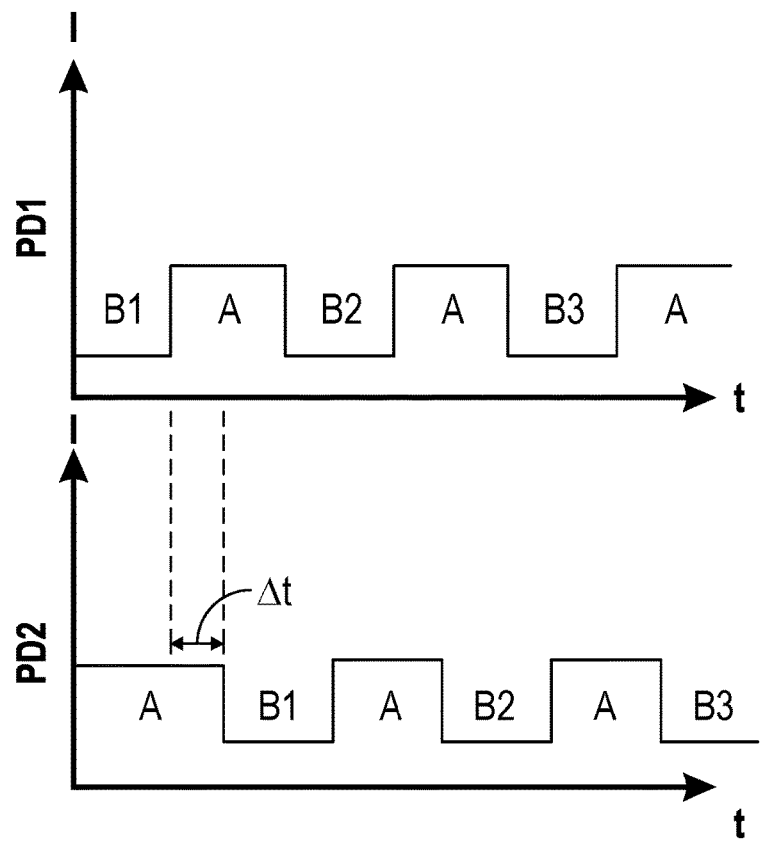
FIG. 7B is a set of graphs illustrating signal waveforms for detectors in the optical flow sensor arrangement depicted in FIG. 7A, according to some example embodiments.

The signal strength output by an optical detector may be used to distinguish between different fluid components of the fluidic content passing through the conduit 750 between the optical detector and its corresponding optical emitter. In the example shown in FIG. 7A, three boluses B1, B2, and B3 of a patient fluid (e.g., blood) are depicted flowing through the conduit 750 between optical emitters and their corresponding optical detectors (e.g., between emitter LED1 and corresponding detector PD1). The boluses B1, B2, and B3 are interspersed with air. As shown in FIG. 7B, the intensity I of the signal from PD1 varies over time (t) as the boluses and interspersed air pass through the conduit 750. Specifically, lower signal intensity corresponds to passage of patient fluid (e.g., boluses B1, B2, and B3) due to the patient fluid's absorption of the emitted light, and higher signal intensity corresponds to passage of air. Accordingly, patient fluid, such as blood, can be distinguished from air based on the signal intensity output by one or more optical detectors. Furthermore, in some variations, the type of non-air fluid (e.g., blood, saline, urine, etc.) may be identified based on the signal intensity from one or more optical detectors, since different fluids may absorb different amounts of light.

As shown in FIG. 7A, at least some of the emitter-detector pairs are axially spaced apart along the conduit 750. For example, a second emitter-detector pair may be located downstream of a first emitter-detector pair. Specifically, the first emitter-detector pair may include a first optical emitter LED1 opposite a first photodetector PD1 that is configured to detect light emitted by the first optical emitter LED1. Similarly, the second emitter-detector pair may include a second optical emitter LED2 opposite a second photodetector PD2 that is configured to detect light emitted by the second optical emitter LED2. Since the second emitter-detector pair is located downstream of the first emitter-detector pair, the second photodetector PD2 detects a segment of fluidic content after the first photodetector PD1 detects the same segment. This temporal offset between the patient fluid detection events in the first and second photodetector PD1 and PD2 signals can be correlated to an estimated flow velocity between the first and second emitter-detector pairs by Equation 3:

$$V = \frac{L}{\Delta t} \qquad (3)$$

where V=flow velocity, L=distance between the first and second emitter-detector pairs, and Δt=temporal offset between patient fluid detection events for the first and second optical detectors (e.g., photodetectors PD1 and PD2). Thus, cross-correlation between the photodetectors PD1 and PD2 can be used to measure flow velocity. In some variations, the addition of a third, fourth, or more axially-spaced emitter-detector pairs may be used for supplemental or added accuracy or precision (e.g., by averaging cross-correlations of different sets of emitter-detector pairs), for verifying the flow velocity measurement (e.g., by checking for variation or redundancy in the time offset), or for both. The volumetric flow rate can then be estimated by, for example, multiplying the flow velocity V with the cross-sectional area A of the fluid in the conduit.

As shown in FIG. 7A in dashed lines, emitted light may undergo refraction when being transmitted through certain media. To account for this refraction and be able to detect refracted light whose incident location on a detector is not directly opposite its emission location, an optical detector in an emitter-detector pair may have a detection region that is wide enough, long enough, or both, to capture refracted light. For example, at least some of the optical detectors may be or function as an area sensor configured to detect light falling onto a two-dimensional (e.g., rectangular) region, or may be a line sensor configured to detect a light falling onto a one-dimensional (e.g., linear) region. Additionally, in some variations, spectroscopic properties of the fluidic content (e.g., determined by spectroscopic analysis, as described below) may be used to quantify the refractive nature of the fluidic content, such as through a look-up table or an equation based on weighted values of the spectroscopic properties. Given that L in Equation 3 above may be affected by the refraction of the fluid, a refractive value representing the refractive nature of the fluidic content can then be used to dynamically adjust the value of L to account for different compositions of fluid passing through the conduit 750. Furthermore, in some variations, the type of fluid (e.g., blood, saline, urine, air, etc.) may be identified based on the incident location of detected light relative to the emission location, since different fluids generally have different indices of refraction.

Figure 8A:
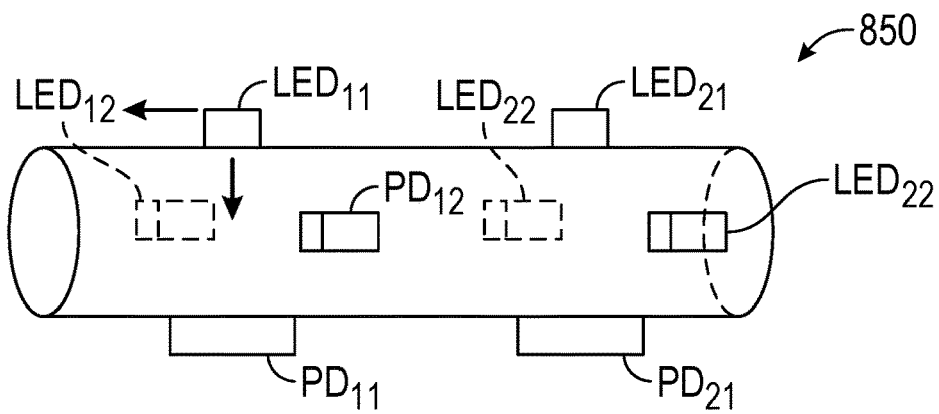
FIG. 8A is a schematic diagram illustrating an optical flow sensor arrangement, according to some example embodiments.

In some variations, the sensor arrangement (e.g., the sensor arrangement 110, 210, or 310) includes emitter-detector pairs arranged at a plurality of circumferential locations around the conduit (e.g., the conduit 120, 250, 450, 550, 650, or 750). For example, as shown in FIG. 8A, a first emitter-detector pair (LED11, PD11) is circumferentially offset from a second emitter-detector pair (LED12, PD12), though the first and second emitter-detector pairs are located at the same approximate axial location. In some variations, to reduce interference between emitter-detector pairs located at the same approximate axial location, each emitter-detector pair at that axial location may operate on a distinct corresponding wavelength. For example, the optical emitter LED11 may be configured to emit light only at a first wavelength, and its corresponding photodetector PD11 may be configured to detect light only at the first wavelength. Similarly, the optical emitter LED12 may be configured to emit light at a second wavelength different from the first wavelength, and the photodetector PD12 may be configured to detect only light at the second wavelength.

Figure 9:
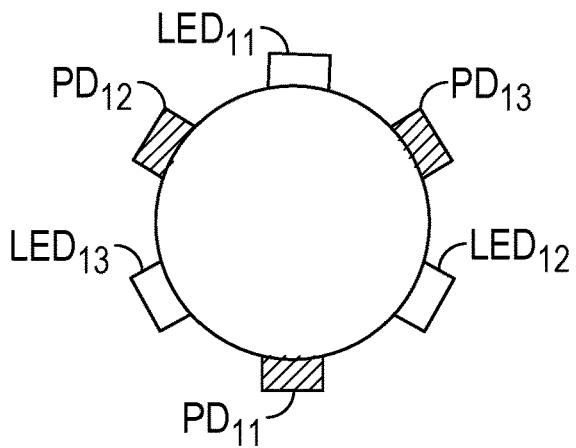
FIG. 9 is a cross-sectional view of another optical flow sensor arrangement, according to some example embodiments.

In some variations, interference between axially-aligned emitter-detector pairs may additionally or alternatively be reduced by alternating the optical emitters and optical detectors. For example, as shown in FIG. 9, a set of three emitter-detector pairs (LED11, PD11), (LED12, PD12), and (LED13, PD13) may be arranged in alternating fashion (e.g., with no two optical emitters immediately adjacent to each other and no two optical detectors immediately adjacent to each other). Accordingly, the photodetector PD11 in the first emitter-detector pair is unlikely to receive light from either the optical emitter LED12 or the optical emitter LED13, respectively from the second and third emitter-detector pairs, for example. Thus, each optical detector will receive substantially only the light emitted from its corresponding optical emitter.

Figure 8B:
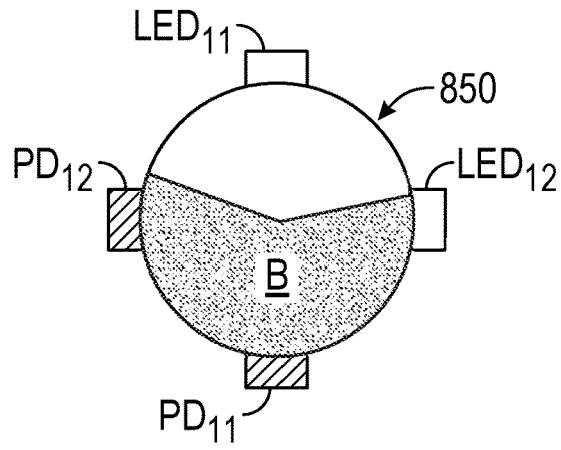
FIG. 8B is a cross-sectional view of the optical flow sensor arrangement depicted in FIG. 8A, according to some example embodiments.
Figure 8C:
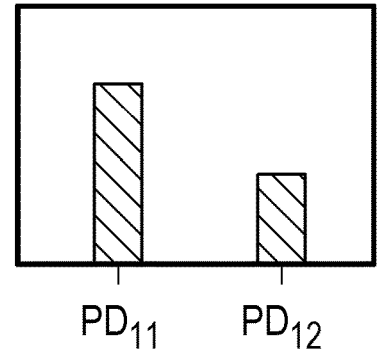
FIG. 8C is a graph illustrating signal intensity for detectors in the optical flow sensor arrangement depicted in FIG. 8B, according to some example embodiments.

FIG. 8B illustrates a cross-section of the sensor arrangement depicted in FIG. 8A, taken at the axial location of the first and second emitter-detector pairs. Circumferentially distributed emitter-detector pairs may enable measurement of the flow rate when the cross-sectional area of a conduit 850 is not completely filled with a non-air fluid. For example, as shown in FIG. 8B, the conduit 850 may be only partially filled with a bolus B of a patient fluid (e.g., blood). In this illustrative example, the bolus B does not traverse the entire distance between a first optical emitter LED11 and its corresponding first photodetector PD11, and the signal from that first photodetector PD11 may not be sufficient to reliably indicate the presence of the bolus B. Thus, the first emitter-detector pair with that first photodetector PD11 may not be sufficient to facilitate reliable flow rate measurements as described above with respect to FIGS. 7A and 7B. However, as shown in FIG. 8B, the bolus B does traverse the entire distance between a second optical emitter LED12 and its corresponding second photodetector PD12, such that the signal from that second photodetector PD12 may be used for flow rate measurements (e.g., alone or together with output from at least one of the downstream emitter-detector pairs (LED21, PD21) and (LED22, PD22)). Thus, such circumferentially-arranged emitter-detector pairs may enable measurement of the flow rate, even if the conduit 850 is only partially filled (e.g., half full). It should be understood that more than two emitter-detector pairs (e.g., three, four, five, or any suitable number) may be arranged circumferentially around the conduit 850 to provide more sensitivity to the presence of non-air fluid in the conduit.

Furthermore, in some variations, the circumferentially arranged optical detectors can inform on the distribution of fluid, the amount of fluid, or both, at their shared axial location on the conduit 850. For example, with reference to FIG. 8B, because the bolus B absorbs less light from the first optical emitter LED11 and absorbs more of the light from the second optical emitter LED12, the signal intensity from the first photodetector PD11 is higher than the signal intensity from the second photodetector PD12. Thus, the relative signal intensities for the first and second photodetectors PD11 and PD12 can indicate the distribution and amount of the patient fluid at the axial location of the first and second photodetectors PD11 and PD12. For example, two orthogonally-arranged emitter-detector pairs can detect whether the conduit is half full or entirely full. More emitter-detector pairs may be arranged circumferentially around the conduit 850 (e.g., at the same axial location on the conduit 850) to provide more resolution in the cross-sectional area of the conduit 850 that contains the fluid being measured.

As described above, the sensor arrangement (e.g., the sensor arrangement 110, 210, or 310) may include optical emitter-detector pairs arranged at a plurality of axial locations along the conduit (e.g., the conduit 120, 250, 450, 550, 650, 750, or 850), at a plurality of circumferential locations around the conduit, or both. For example, as shown in FIG. 8A, at least some of a plurality of emitter-detector pairs may be arranged in a series of axially spaced-apart rings. As another example, at least some of a plurality of emitter-detector pairs may be arranged helically around the conduit. A helical arrangement may, for example, help avoid optical interference between adjacent emitter-detector pairs.

Example Thermal Mass Flow Sensor

Figure 10:
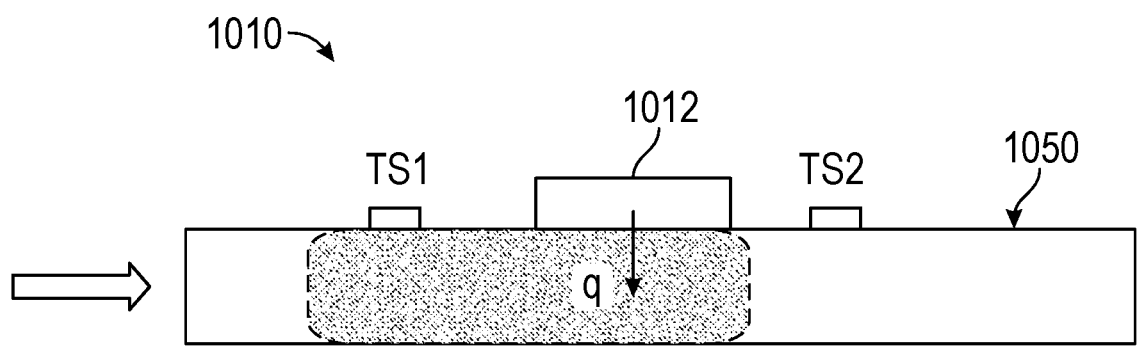
FIG. 10 is a schematic diagram illustrating a thermal mass flow sensor, according to some example embodiments.

In some variations, as shown in FIG. 10, the sensor arrangement (e.g., the sensor arrangement 110, 210, or 310) includes a thermal mass flow sensor 1010 configured to quantify the mass of fluidic content flowing through a conduit 1050. For example, estimating a thermal mass flow of the fluidic content can include introducing a known amount of heat into the flow of fluidic content and measuring the associated (e.g., corresponding) temperature change in the fluidic content. This may be performed, for example, by maintaining a probe at a constant temperature and measuring the energy consumed in doing so. As another example, estimating a thermal mass flow of the fluidic content can include introducing a known amount of heat into the flow of fluidic content and measuring the change in temperature of the fluidic content at some point downstream.

For example, as shown in FIG. 10, the sensor arrangement (e.g., the sensor arrangement 110, 210, or 310) may include at least a first temperature sensor TS1 and a second temperature sensor TS2 located downstream of the first temperature sensor TS1. The first and second temperature sensors TS1 and TS2 may, for example, be based on microelectromechanical systems (MEMS). One or more heat sources 1012, such as a heating coil or other suitable heating element, may introduce a known amount of heat energy into the fluidic contents of the conduit 1050 (e.g., through the wall of the conduit 1050) between the first and second temperature sensors TS1 and TS2. The difference in temperature measurements by the first and second temperature sensors TS1 and TS2 as a result of the heating of the fluidic contents in the conduit 1050 can be correlated to a measurement of mass flow, according generally to Equation 4:

$$m = \frac{Kq}{C_p(T_2 - T_1)} \quad (4)$$

where m=mass flow, K=a conduit constant, $C_p$=specific heat of fluidic contents of the conduit 1050, $T_2$=temperature measurement by the second temperature sensor TS2, and $T_1$=temperature measurement by the first temperature sensor TS1. The value of K may be known or looked up based on properties of the conduit 1050 (e.g., tubing material, tubing wall thickness, tubing diameter, etc.), or may be determined based on previous experimental data, for example. The value of K may be manually entered (e.g., by a user), recorded in and received from a computer-readable storage medium, automatically recognized by the system 100, such as through optical character recognition of a label on the conduit 1050 or another suitable reference code, or any suitable combination thereof. In some variations, the value of K may be derived from an optical or electrical resistance sensor, where the sensor output can be used to determine the K value (e.g., via a look-up table, an equation, etc.). Multiple methods for determining the K value can be combined (e.g., averaged) or used for redundancy purposes. The specific heat of fluidic contents of the conduit 1050 may be a constant value that is known or assumed as representative of a known fluid passing through the conduit 1050. However, in some variations, the value of $C_p$ may vary depending on other factors. For example, the value of $C_p$ may depend on the composition of the fluidic content (e.g., by weight averaging respective specific heat values for each fluid component), which may be determined with spectroscopic analysis, for example, as described below. Once composition of the fluidic content is determined, a look-up table, heuristically-derived equation, other suitable tool, or any suitable combination thereof, may be used to determine a suitable value of $C_p$ in Equation 4.

In some variations, one or more heat sources 1012 (e.g., heating coils or other heating elements) may be positioned on or adjacent to an external surface of the conduit 1050. For example, a heating element may be mounted in a housing (e.g., the housing 220) of the sensor arrangement (e.g., the sensor arrangement 110, 210, or 310), such that when the conduit 1050 is received in the housing, the conduit 1050 is self-aligning and contacts the heating element. In other variations, one or more heating elements may be integrated in the material of the conduit 1050 so as to more directly heat the fluidic contents in the conduit 1050.

Although two temperature sensors (e.g., the first and second temperature sensors TS1 and TS2) are depicted in FIG. 10, it should be understood that three, four, five, or more temperature sensors may be included to measure thermal mass flow. For example, an array of temperature sensors (e.g., with one or more heating elements) may be arranged at a plurality of axial locations, at a plurality of circumferential locations (e.g., in a series of rings, in helical fashion, etc.), or both. Like arrangements of optical flow sensors as described above, the combination of axial and circumferential arrangements of thermal mass flow sensors may enable averaging of thermal mass flow results, verifying of thermal mass flow results, or both. Furthermore, such combined arrangements can provide thermal mass flow measurements under a greater variety of fill conditions (e.g., when the conduit 1050 is partially filled or fully filled).

In some variations, any of the optical flow sensor arrangements and any of the thermal mass flow sensor arrangement described above may be combined to enable quantification of flow across a wider range of conditions. For example, optical flow sensors may be more accurate quantifying flow (e.g., estimating the flow rate) within the conduit (e.g., the conduit 120, 250, 450, 550, 650, 750, 850, or 1050), when the flow is intermittent (e.g., includes boluses of liquid interspersed with air), while thermal mass flow sensors may be more accurate quantifying flow (e.g., estimating the thermal mass flow) when the flow is continuous. Accordingly, use of optical flow sensors and thermal mass flow sensors together may enable accurate quantification of flow in a conduit across a wider range of flow conditions (e.g., both intermittent and continuous flow) in the conduit, such that the system 100 is even more robust despite unpredictable flow conditions. Furthermore, in some variations, the fluidic content may not need to be preprocessed to have predetermined characteristics (e.g., moving in laminar flow) in order for the system 100 to accurately quantify patient fluid loss.

Example Color Image Flow Sensor

In yet other variations, the sensor arrangement (e.g., the sensor arrangement 110, 210, or 310) includes one or more image sensors configured to quantify flow, estimate composition or component concentration of the fluidic content in the conduit (e.g., the conduit 120, 250, 450, 550, 650, 750, 850, or 1050), or both. For example, an optical image sensor (e.g., CCD, CMOS, etc.) may capture a color optical digital image with red, green, and blue (RGB) color components for the pixels (e.g., along with other suitable optical components). For example, the image sensor may be a single image sensor paired with suitable corresponding optics, filters (e.g., color filter arrays such as a Bayer pattern filter), or any suitable combination thereof. As another example, the sensor arrangement may include multiple image sensors paired with suitable corresponding optics, such as at least one prism or diffractive surface to divide white light into separate color channels, each of which is detected by a respective image sensor (e.g., with an appropriate optical filter corresponding to a color channel). However, the sensor arrangement may include any suitable image sensors and other optical components to enable the sensor arrangement to generate images of the conduit and its fluidic content.

A machine learning algorithm (e.g., a neural network or other suitable algorithm) may be applied to the image data to distinguish between different kinds of flow such as laminar, turbulent, and air in the conduit (e.g., the conduit 120, 250, 450, 550, 650, 750, 850, or 1050). For example, a machine configured in accordance with such a machine learning algorithm may be trained to classify flow using experimentally derived training data. Images of the fluidic content of the conduit may then be provided as inputs to the trained machine (e.g., trained by inputting the training data into the machine learning algorithm). In some variations, the trained machine can analyze color component values (e.g., RGB, CYMK, or other suitable color space) to determine areas of the conduit likely to be air, laminar flow, turbulent flow, etc. By identifying features in the image of the fluidic content, the trained machine may additionally or alternatively quantify aspects of the flow (e.g., flow rate) within the conduit. Other example methods of characterizing fluid in a conduit by analyzing color images of the fluid are described in U.S. Patent Publication No. 2016/0335779, which was incorporated by reference above.

Additionally or alternatively, color component information may be correlated to composition of the fluidic content. For example, the concentration of a fluid component of the fluidic content can be determined from color component pixel values using methods described in U.S. Pat. No. 8,792,693, which was incorporated by reference above. In some variations, the same one or more color image sensors may be used to quantify flow of fluidic content (e.g., as described above) and estimate an aspect of the composition of the fluidic content. In some variations, a machine learning algorithm (e.g., a neural network or other suitable algorithm) may be applied to the image data to identify constituent fluid components of the fluidic content in the conduit (e.g., the conduit 120, 250, 450, 550, 650, 750, 850, or 1050). For example, a machine configured in accordance with such a machine learning algorithm may be trained using experimentally-derived training data. Images of the fluidic content of the conduit may then be provided as inputs to the trained machine (e.g., trained by inputting the training data into the machine learning algorithm). In some variations, the trained machine can analyze color component values (e.g., RGB, CYMK, other suitable color space) to determine color-related pixel values that are correlated to various fluid components (e.g., with the intensity of the red channel for a pixel correlated to blood). By identifying features in the image of fluidic content, the trained machine can identify information about relative amounts of fluid types, relative concentrations of fluid components, etc. within the conduit.

Example Multispectral Image Sensor

Figure 11:
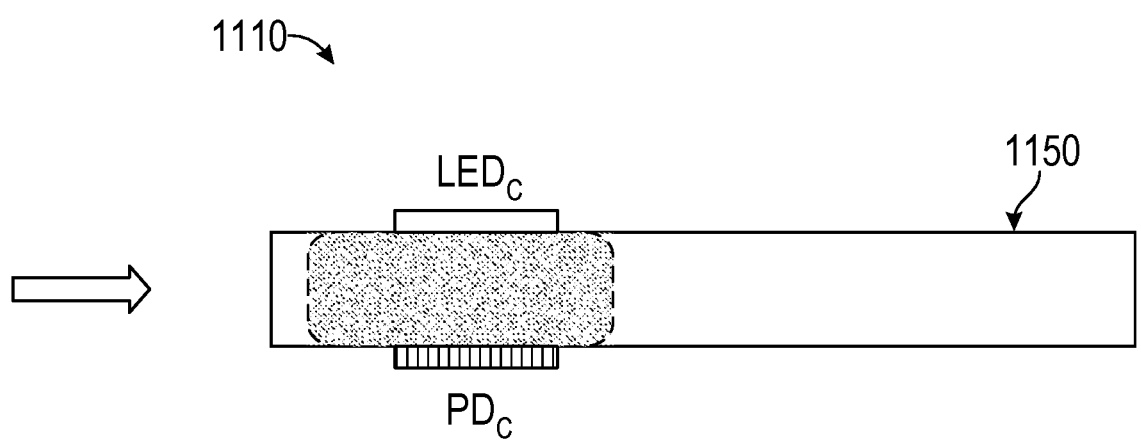
FIG. 11 is a schematic diagram illustrating a multispectral imaging arrangement, according to some example embodiments.

In some variations, the sensor arrangement (e.g., the sensor arrangement 110, 210, or 310) further includes one or more sensors configured to estimate the concentration of one or more fluid components of the fluidic content, other composition of the fluidic content of the conduit (e.g., the conduit 120, 250, 450, 550, 650, 750, 850, or 1050), or both. For example, as shown in FIG. 11, the sensor arrangement may include a multispectral imaging arrangement 1110 that includes a multispectral emitter array LEDc configured to emit a range of wavelengths of light, and a multispectral detector array PDc configured to detect a range of wavelengths of light reflected by the fluidic content in a conduit 1150. For example, the multispectral emitter array LEDc, which may include LEDs or other suitable optical emitters, may be configured to emit light generally in the visible spectrum, the near infrared spectrum, or both (e.g., emit light generally having wavelengths between 400 nm and 900 nm). The multispectral emitter array LEDc may include multiple LEDs, each emitting light of a subset of the range of wavelengths (e.g., 400 nm-450 nm, 450 nm-500 nm, etc.), such that collectively the emitter array LEDc emits the suitable multispectral range. The multispectral detector array PDc, which may include CMOS sensors or ocher suitable image sensors, may also be configured to detect light generally in the visible spectrum, the infrared spectrum, or both. For example, the multispectral detector array PDc may include multiple CMOS sensors, each sensor having a corresponding filter, such that each CMOS sensor detects only wavelengths of light permitted by the filter. In an example embodiment, the multispectral imaging arrangement 1110 includes between about 10 and about 100 LEDs (e.g., in the emitter array LEDc) and between about 10 and 100 CMOS sensors (e.g., in the detector array PDc). Each LED may emit a respective discrete range of wavelengths of light, and may have a corresponding CMOS sensor that detects the same range of wavelengths of light.

Various aspects of the composition of the fluidic content can be measured by analyzing the detector signals from the multispectral imaging arrangement 1110 in spectroscopic analysis. Specifically, since different kinds of matter absorb or reflect different wavelengths of light, the spectral pattern measured by the multispectral detector array PDc can be analyzed to characterize the composition of the fluidic content. In some variations, the relative amounts (e.g., concentrations) of fluid types present (e.g., blood, urine, saline, etc.) can be determined by analyzing the signals from the detector array PDc. For example, blood generally has an absorption spectra peak of about 530 nm. Accordingly, signal from a sensor in the multispectral detector array PDc that detects light at 530 run may be correlated to the amount of blood that is in the conduit 1150. As another example, urine generally has an absorption spectra peak of about 430 nm, such that signal from a sensor in the multispectral detector array PDc that detects light at 430 nm may be correlated to the amount of urine that is in the conduit 1150. In some variations, the signals from the multispectral detector array PDc may be processed through spectroscopic analysis to determine the concentration of a fluid component (e.g., hemoglobin) among other fluid components in the fluidic content. Furthermore, in some variations, the same sensor signals may be processed through spectroscopic analysis to determine level of hemolysis, so as to obtain a measure of amount of whole blood relative to hemolyzed blood.

For fluid in the conduit 1150 having multiple fluidic components, the unscattered absorbance for each of the total of n fluidic components (n=1, 2, 3, . . . ) may be summed to provide a total absorbance $\Sigma A$ that is directly measured by the multispectral imaging arrangement 1110 at different wavelengths, for example according to Equation 5:

$$\Sigma A(\lambda) = \Sigma_{i=1}^{n} \in_i(\lambda) c_i d_i \tag{5}$$

where $\in_i(\lambda)$ is the absorptivity (known for many substances), $c_i$ is the concentration (to be determined), and $d_i$ is the optical path length in each fluid component in the conduit 1150. By measuring the total absorbance at n or more wavelengths of light, the system 100 can determine the concentration of each of the constituent fluid components of the fluidic content in the conduit 1150, such as according to Equations 6:

$$\varepsilon_1(\lambda_1)c_1d_1 + \varepsilon_2(\lambda_1)c_2d_2 + \cdots + \varepsilon_n(\lambda_1)c_nd_n = \sum A(\lambda_1) \tag{6}$$
$$\varepsilon_1(\lambda_2)c_1d_1 + \varepsilon_2(\lambda_2)c_2d_2 + \cdots + \varepsilon_n(\lambda_2)c_nd_n = \sum A(\lambda_2)$$
$$\vdots$$
$$\varepsilon_1(\lambda_n)c_1d_1 + \varepsilon_2(\lambda_n)c_2d_2 + \cdots + \varepsilon_n(\lambda_n)c_nd_n = \sum A(\lambda_n)$$

Thus, all the fluidic component concentrations can be estimated by putting the above Equations 6 in matrix form and performing mathematical operations on the matrix (e.g., by obtaining a least-square estimate).

Other variations of the sensor arrangement (e.g., the sensor arrangement 110, 210, or 310) include any suitable combination of the above-described sensors (e.g., ultrasound, optical, thermal, color image, and multispectral image), which may be used to quantify flow of fluidic content through a conduit (e.g., the conduit 120, 250, 450, 550, 650, 750, 850, 1050, or 1150), estimate composition of the fluidic content (e.g., estimate a fluidic component concentration), or both. For example, analysis of data from multiple sensors can be averaged or otherwise combined in a fusion algorithm to improve accuracy. Furthermore, use of multiple sensors can provide redundancy, such that failure of one sensor, for example, might not render the system 100 inoperable. As another example, as described above in a few examples, multiple measuring modalities can improve sensitivity, reliability, or both, of the measurements across a wider range of flow conditions (e.g., turbulent or laminar, continuous or intermittent, mixed fluid types, etc.). Furthermore, in some variations, a single sensor arrangement (e.g., a color image sensor arrangement) may provide sufficient data to enable both quantifying flow and estimating concentration of one or more fluid components, as described above.

Example Processor and Example Memory Components

Generally, the system 100 may include one or more processors configured to execute instructions that are stored in memory, such that, when the one or more processors execute the instructions, the one or more processors performs aspects of the methods described herein. For example, the one or more processors may be configured to quantify flow of fluidic content through a conduit (e.g., the conduit 120, 250, 450, 550, 650, 750, 850, 1050, or 1150), estimate a concentration of a fluid component in a patient fluid, characterize patient fluid loss based at least in part on the quantified flow and the concentration of the fluid component, or any suitable combination thereof. Other aspects of data analysis may additionally be performed by the one or more processors.

In an example variation, the system 100 estimates the amount of patient blood that has been collected and passed through the conduit, based at least in part on the sensor measurement described above. For example, the mass of hemoglobin that has passed through the conduit over a measurement period of time can be estimated by multiplying the blood volumetric flow rate through the conduit to the concentration of hemoglobin in the conduit, as measured during the measurement period of time. The volumetric flow rate of blood can be determined based on overall flow rate (e.g., as quantified by the one or more sensors described above) and the relative amount of blood compared to other fluid types in the conduit (e.g., as measured with spectroscopic or optical analysis as described above). The concentration of hemoglobin can be measured with spectroscopic or optical analysis, as described above. Furthermore, patient blood loss can be estimated by dividing the estimated hemoglobin mass loss by a known serum-derived patient hemoglobin value. The estimated patient blood loss over the measurement period of time can be aggregated over multiple measurement periods of time as a running patient blood loss total, aggregated with other estimations based on other fluid collection sources such as surgical textiles, as described above, or both. Such patient blood loss metrics can be indicated to a user, such as through a display or audio device, as described in further detail below. In some variations, the estimated hemoglobin mass itself may be a metric characterizing patient fluid loss. Furthermore, in some variations, any of the methods described herein may be applied to determine the concentration and flow rate of other bodily fluids (e.g., urine, amniotic fluid, spinal fluid, bile) through a conduit. The measured values can be aggregated over multiple measurement periods of time as a running fluid loss total, aggregated with other estimations based on other fluid collection sources, as described above, or both.

Referring back to FIG. 1, one or more processors 154 may, for example be located in a computing device 150, which may be remote computing device relative to the sensor arrangement 110. Examples of the one or more processors 154 are further described below with respect to FIG. 18. The computing device 150 may be or include a handheld or mobile device (e.g., a tablet computer, laptop computer, mobile smartphone, etc.). The instructions discussed above may be executed, for example, by computer-executable components integrated with an application, applet, host, server, network, website, communication service, communication interface, hardware elements, firmware elements, software elements, wristband, smartphone, or any suitable combination thereof. In some example embodiments, the instructions may be performed at least in part by one or more processors that are separate from the computing device 150 (e.g., on-site in the operating room or remotely outside the operating room), such as a cloud-based computer system, a mainframe computer system, a grid-computer system, or other suitable computer system.

The instructions may be stored on memory 152 of the computing device 150 or other computer-readable medium such as RAMs, ROMs, flash memory, EEPROMs, optical devices (e.g., CD or DVD), hard drives, floppy drives, or any suitable storage device. Examples of the memory 152 are further described below with respect to FIG. 18. Additionally or alternatively, one or more processors may be located in or near the sensor arrangement 100 for local analysis.

Furthermore, sensor data, results of any analysis performed by a local processor at the sensor arrangement 110, or both, may be communicated in a wired or wireless connection (e.g., via WiFi, Bluetooth, Zigbee, Airdrop, etc.) with a remote computing device, such as the computing device 150 shown in FIG. 1. In some variations, one or more local memory components, similar to those described above, may be included in the sensor arrangement 110 in order to store a queue or backlog of such data. This queue or backlog may, for example, provide a buffer of stored data to avoid loss of data in the event that data transfer to the computing device 150 is interrupted or otherwise fails.

Example User Interactive Components

In some variations, as shown in FIG. 1, the system 100 may further include one or more displays 148 configured to display data, an analysis of the data (e.g., estimation of patient fluid loss) to a user, or both. The display 148 may include a screen on a handheld or mobile device (e.g., as part of the same computing device 150 as the one or more processors 154 described above), a computer monitor, a television screen, a projector screen, or other suitable display. In some variations, the display 148 is configured to display a user interface (e.g., a graphical user interface) that enables the user to input information (e.g., a serum-derived patient hemoglobin value, or conduit tube information, such as brand, material, size, wall thickness, etc., which may be used to calibrate the system 100 to a specific conduit type), select display options (e.g., font, color, language, etc.), display content (e.g., patient information, fluid-related information, alerts, etc.), or any suitable combination thereof. In such variations, the display 148 may be user-interactive and include a resistive or capacitive touch screen that is responsive to skin, a stylus, or other user contact. In other variations, the display 148 may be user-interactive via a cursor controlled by a mouse, keyboard, or other suitable input device.

In some variations, the system 100 may additionally or alternatively include an audio system 156 configured to communicate information (e.g., fluid-related information, alerts, etc.) to a user. For example, the display 148, the audio system 156, or both, may provide alerts or alarms upon the estimated quantity of trend of fluid loss meeting a threshold, which may be useful to prompt certain actions in response, such as providing a blood transfusion to the patient.

The descriptions herein, for purposes of explanation, use specific nomenclature to provide a thorough understanding of the present subject matter. However, it will be apparent to one skilled in the art that specific details are not required in order to practice the present subject matter. Thus, the descriptions of specific example embodiments (e.g., variants or variations) of the present subject matter are for purposes of illustration. They are not intended to be exhaustive or to limit the subject matter to the precise forms disclosed, as many modifications and variations are possible in view of the above teachings. The example embodiments described herein explain the innovations involved and their practical applications, and they thereby enable others skilled in the art to utilize the present subject matter and various example embodiments thereof with various modifications as suited to the particular use contemplated.

Example System Modules

Figure 12:
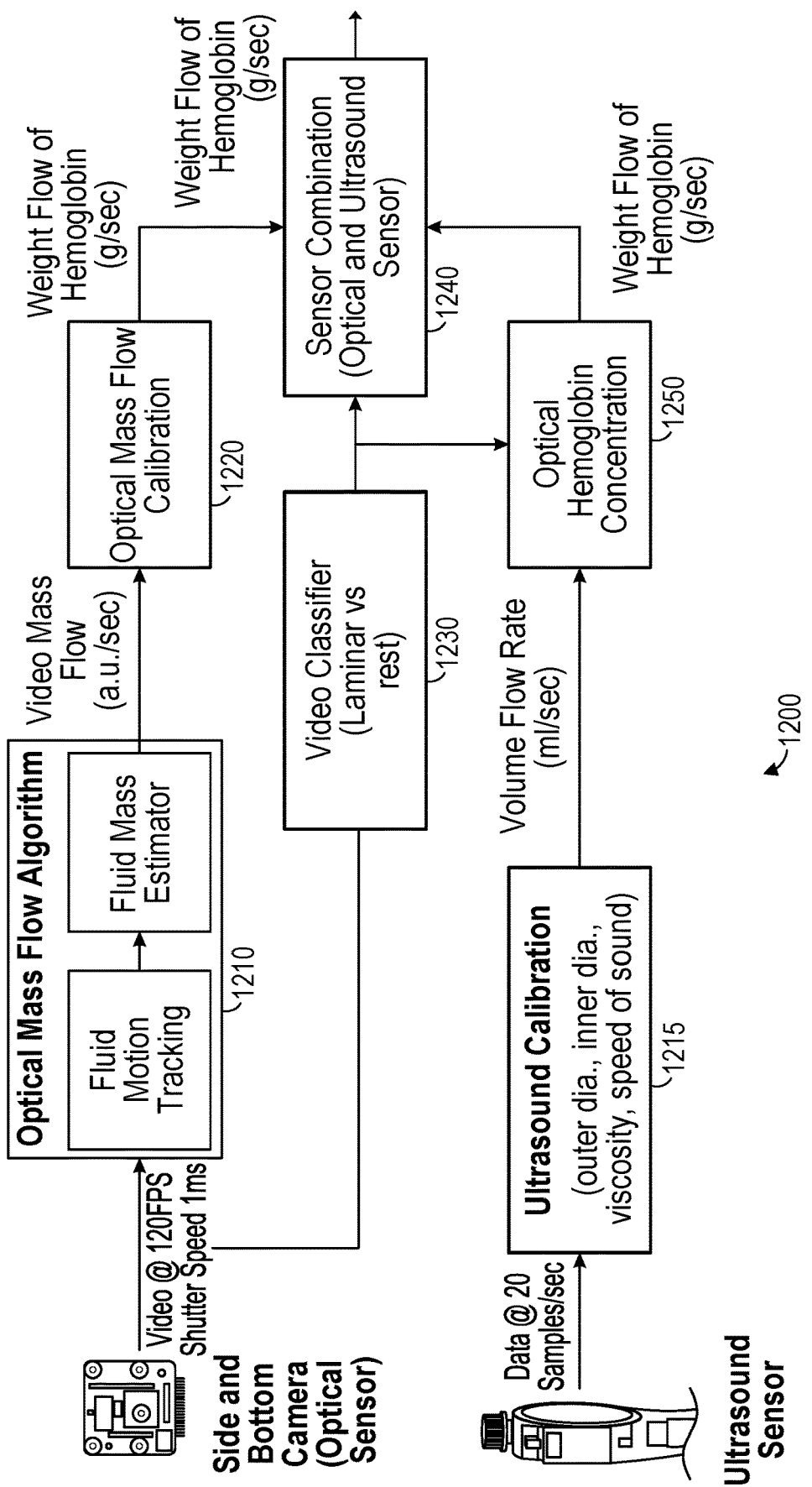
FIG. 12 is a flowchart illustrating operation of a system in performing a method of characterizing fluidic contents flowing through a conduit, according to some example embodiments.

FIG. 12 is a flowchart illustrating operation of the system 100 in performing a method 1200 of characterizing fluidic contents flowing through a conduit (e.g., the conduit 120, 250, 450, 550, 650, 750, 850, 1050, or 1150), according to some example embodiments. In such example embodiments, images (e.g., video images) of the fluidic content flowing through the conduit are captured by an optical sensor (e.g., a camera) and are inputted into an optical mass flow algorithm 1210, which is shown as including fluid motion tracking followed by fluid mass estimation. The output of the optical mass flow algorithm 1210 is processed by an optical mass flow calibration operation 1220, and the resultant output is provided to a sensor combining operation 1240.

On a separate path, the images of the fluidic content are also provided as input to a video classifier 1230, which may be configured to distinguish laminar flows from non-laminar flows. The output of the video classifier 1230 is also provided to the sensor combining operation 1240. In addition, the output of the video classifier 1230 may serve as input to an optical hemoglobin concentration detector 1250, whose output feeds the sensor combining operation 1240.

Furthermore, sensor data from an ultrasound sensor is accessed and provided as input to an ultrasound calibration operation 1215, and the resultant output is fed as input to the optical hemoglobin concentration detector 1250. As noted above, the output from the optical hemoglobin concentration detector 1250 is provided to the sensor combining operation 1240.

The sensor combining operation 1240, thus, combines its inputs to obtain the concentration of the fluid component (e.g., hemoglobin) of the patient fluid (e.g., blood) included in the fluidic contents flowing through the conduit. Moreover, with the combined inputs based on multiple types of sensor data (e.g., video data and ultrasonic data), the sensor combining operation 1240 outputs accurate results under a wide variety of flow conditions for the fluidic content in the conduit. Examples of such conditions include regions of continuous flow, regions of non-continuous flow (e.g., intermittent flow or otherwise irregular flow), regions of laminar flow, and regions of turbulent flow, as well as any suitable combinations thereof.

Figure 13:
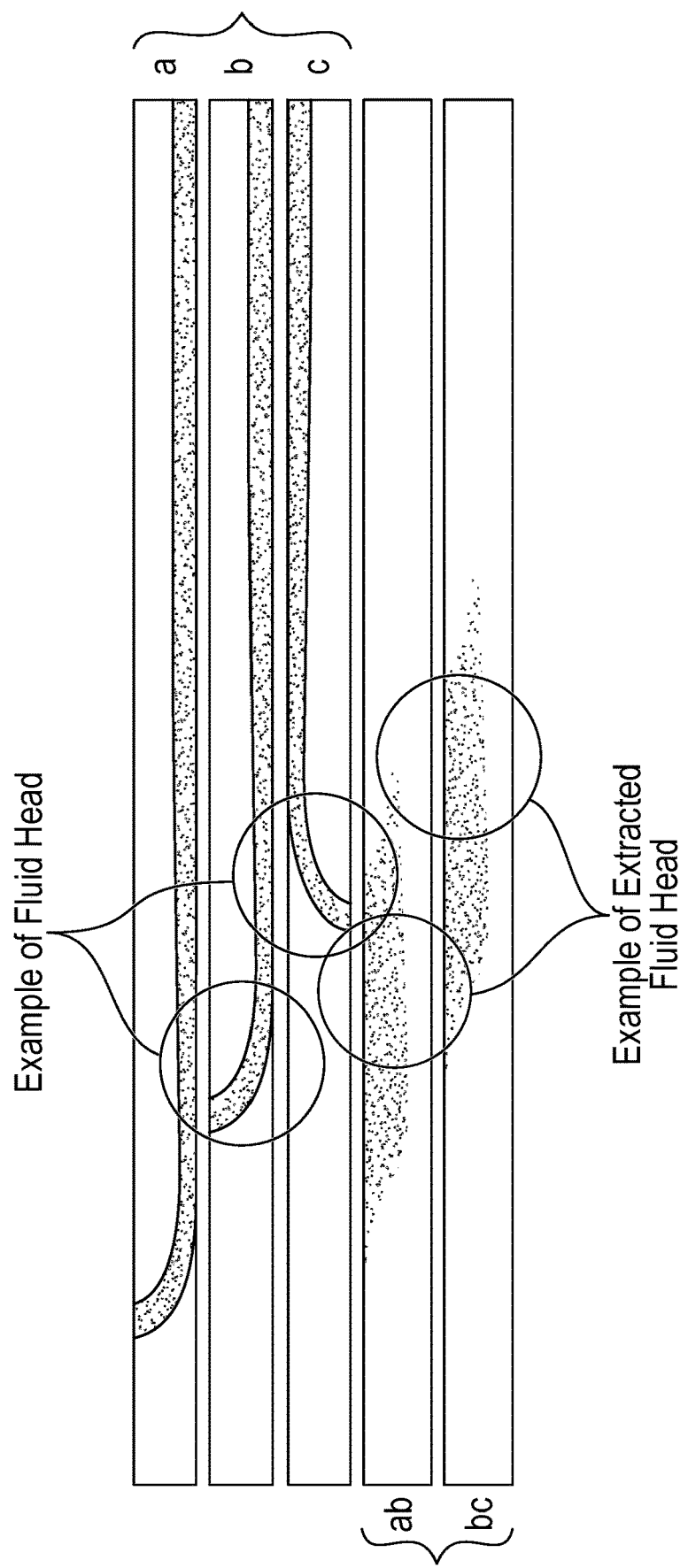
FIG. 13 is a diagram illustrating motion tracking of fluidic content, according to some example embodiments.

FIG. 13 is a diagram illustrating motion tracking of fluidic content, according to some example embodiments. As shown in FIG. 13, when fluidic content passes through the conduit, the attenuation of light due to absorption results in an optical signature that can be tracked with one or more optical sensors placed along the conduit to determine the motion of the moving fluid in pixel/sec.

Accordingly, the system 100 may include a feature extraction module (e.g., within the sensor arrangement 110, the computing device 150, or any suitable combination thereof) that is or includes an algorithmic module configured to access the digital signal from an optical sensor or optical measurement modality as the input and return a set of digital signals that represent one or more distinctive characteristics of the fluid for algorithmic analysis.

The feature extraction module extracts distinctive characteristics in a moving fluid. Extractable features include but are not limited to (i) moving fluid head, (ii) moving fluid tail, (iii) moving bubbles, (iv) other moving patterns or gradients, and (v) other spatial or temporal cues of movement (e.g. textures associated with movement, temporal variation relative to spatial variation, blurriness, etc.).

In some variations, the feature extraction module extracts features in two-dimensional (2D) space by computing the difference from two consecutive optical sensor data in chronological order. The extracted 2D differential features will be further categorized into sub-categories with a computer vision algorithm or other machine learning algorithm (e.g., a deep learning algorithm).

In some variations, the feature extraction module extracts features in one-dimensional (1D) space by rearranging 2D digital data into 1D digital data before performing the differential feature extractions and categorization.

In some variations, the feature extraction module extracts features in multi-dimensional space by processing multiple digital data from more than one source. Multi-dimensional features, such as three-dimensional (3D) features will be extracted and categorized by computer vision algorithms or other variations of machine learning algorithms.

In some variations, the feature extraction module classifies and segments the feature from optical sensor output using a deep learning model.

Figure 14:
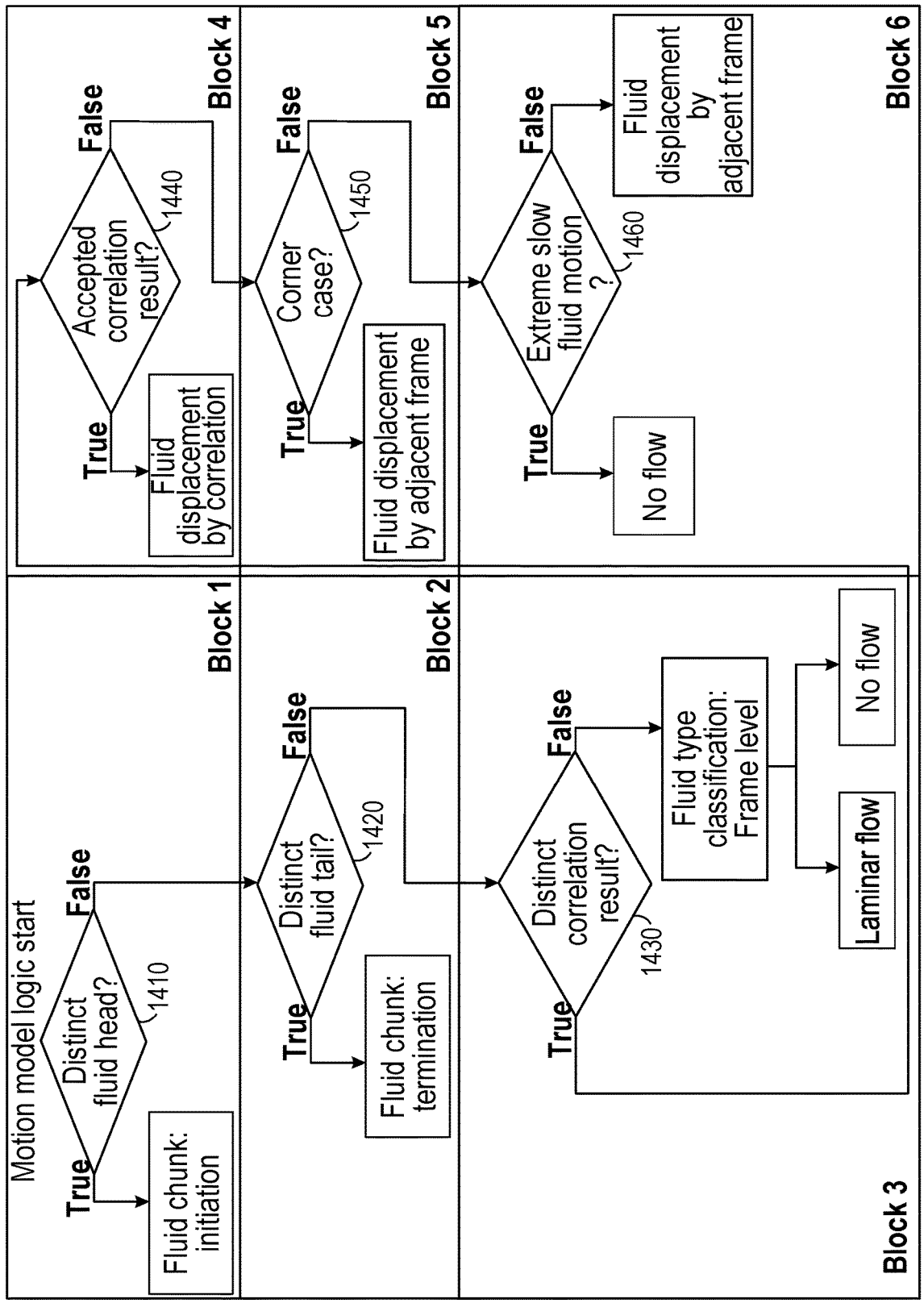
FIG. 14 is flowchart illustrating logical operations in characterizing fluidic content flowing through a conduit, according to some example embodiments.

FIG. 14 is flowchart illustrating a method of performing logical operations in characterizing fluidic content flowing through a conduit, according to some example embodiments. Although this method is described, by way of example, as being performed by the system 100, the method may be performed by other hardware configurations. Accordingly, the system 100 may include a fluid displacement estimation module (e.g., within the sensor arrangement 110, the computing device 150, or any suitable combination thereof) that is or includes an algorithmic module configured to access the extracted feature and compute the displacement of fluid from one point in time to another point in time.

In some variations, the fluid displacement estimation module utilizes mathematical methods to compute the displacement of individual extracted features from different timestamps. Cross-correlation or any other similar mathematical method is used to calculate the shift of the given feature in pixel/sec.

In some variations, the fluid displacement estimation module deploys a deep learning model to estimate fluid displacement from one or multiple optical sensors.

The system 100 may also include a fluid motion model module (e.g., within the sensor arrangement 110, the computing device 150, or any suitable combination thereof) that is or includes an algorithmic module configured to estimate the flow of the fluidic content when there are no strong features to track during a session of the fluid flow, such as during laminar or continuous patches of fluid flow.

The fluid motion model module interpolates the motion of the fluidic content when the fluid displacement module did not output a confident result, such as in a laminar flow session, where there is little to no distinct features for mathematical computation. The fluid motion model module estimates displacement of the fluid from past fluid features, future fluid features (e.g., predicted fluid features), or both.

In some variations, the fluid motion model module is controlled by internal parameters, including but not limited to cross-correlation strength, feature size, and fluid occupancy. As shown in FIG. 14, the fluid motion model module runs through multiple logic blocks (e.g., Block 1, Block 2, Block 3, Block 4, Block 5, and Block 6, or any suitable subset thereof) to determine the confidence of the estimation from fluid displacement estimation module, as well as to re-estimate the fluid displacement with past and future (e.g., predicted) events.

In Block 1, according to some example embodiments, a decision 1410 (e.g., a first decision) is made to determine whether a distinct fluid head is present. If present, the start of a fluid chunk is indicated by the fluid head. Otherwise, no fluid head is present, and the fluid motion model proceeds to Block 2.

In Block 2, according to some example embodiments, a decision 1420 (e.g., a second decision) is made to determine whether a distinct fluid tail is present. If present, the end of a fluid chunk is indicated by the fluid tail. Otherwise, no fluid head or fluid tail is present, and the fluid motion model proceeds to Block 3.

In Block 3, according to some example embodiments, a decision 1430 (e.g., a third decision) is made to determine whether a distinct correlation result is present. If present, the fluid motion model proceeds to Block 4. Otherwise, with no fluid head or fluid tail present, and with no distinct correlation result present, a classification of fluid type is made to distinguish between laminar flow and no flow.

In Block 4, according to some example embodiments, a decision 1440 (e.g., a fourth decision) is made to determine whether the distinct correlation result is accepted. If accepted, the fluid displacement is indicated by the correlation result. Otherwise, the fluid motion model proceeds to Block 5.

In Block 5, according to some example embodiments, a decision 1450 (e.g., a fifth decision) is made to determine whether a corner case (e.g., an exotic, erroneous, or otherwise specially excepted condition) is present. If present, the fluid displacement is indicated by an adjacent image (e.g., the next or previous video image in a sequence of video images that depict the fluidic content in the conduit). Otherwise, the fluid motion model proceeds to Block 6.

In Block 6, according to some example embodiments, a decision 1460 (e.g., a sixth decision) is made to determine whether extreme slow motion of the fluidic content (e.g., with apparent displacement below a threshold of detection) is present. If extreme slow motion is present, the fluid displacement is treated as no flow (e.g., zero displacement from image to image or displacement below a threshold amount from image to image) by the fluid motion model. Otherwise, the fluid displacement is indicated by an adjacent image (e.g., the next or previous video image in a sequence of video images that depict the fluidic content in the conduit), which is likely to show more discernable apparent displacement than the current image.

Figure 15:
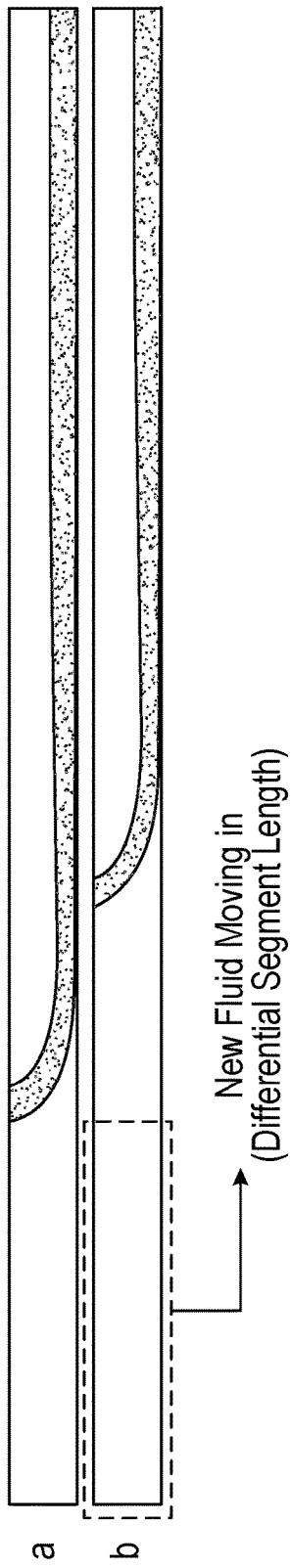
FIG. 15 is a diagram illustrating optical mass estimation for fluidic content, according to some example embodiments.

FIG. 15 is a diagram illustrating optical mass estimation for fluidic content, according to some example embodiments.

The system 100 may include an optical mass estimation module (e.g., within the sensor arrangement 110, the computing device 150, or any suitable combination thereof) that is or includes an algorithmic module configured to analyze the measured substance in the fluidic content when the fluidic content is passing through a conduit (e.g., the conduit 120, 250, 450, 550, 650, 750, 850, 1050, or 1150) paired with a sensor arrangement (e.g., the sensor arrangement 110, 210, or 310) with optical sensors (e.g., CMOS or CCD) and LEDs. The measured substance can be a fluid component of the fluidic content, and the fluid component may be a homogeneous fluid or a heterogeneous fluid, or may have other fluid characteristics.

Assembly of the optical mass estimation module may generally involve placing one or more LEDs or other light sources with different intensities, wavelengths, orientations, or any suitable combination thereof, at one end of a conduit segment (e.g., the conduit segment 350) and one or more photodetectors or other optical sensors with the same or different configurations at the other end of the conduit segment. The optical mass estimation module may first measure the absorbance or transmittance and then utilize physical principles to analyze the target substance (e.g., by applying Beer Lambert's Law to estimate the concentration of the measured substance given its transmittance).

In some variations, multiple pairs of light sources and optical sensors are utilized. For each optical sensor looking toward the conduit segment (e.g., the conduit segment 350), a light source is placed 180 degrees at the opposite side of the conduit segment. The optical mass estimation module estimates the amount of light that is absorbed by the fluidic content that entered the region of interest of the conduit segment, which may be called the differential segment. The optical mass estimation module uses the motion tracking algorithm to determine the length of the differential segment, quantifies the average light absorbance in the differential segment, and applies a mathematical derivation based on Beer-Lambert's Law.

$$A(\delta V)=a(\lambda)dc(\delta V)\propto \delta m_h(t) \qquad (7)$$

where A is absorbance we compute, $\delta V=\pi d^2 \delta p$ is the differential volume, and $\delta p$ is the differential segment length. The system 100 uses Beer Lambert's law to express absorbance in terms of absorptivity $a(\lambda)$ of the measured substance, times the path length d times the concentration c of measured substance in the fluid.

The optical mass estimation module then multiplies the computed absorbance to the length (in pixels) of the differential segment to obtain an optical mass estimation per frame in arbitrary units (a.u.). The optical mass estimation module also integrates the optical mass estimation per frame to obtain an optical mass estimation over time in arbitrary units (a.u.).

In some variations, the optical mass estimation module also estimates the optical mass of the measured substance with one or multiple combinations of LEDs or other light sources, optical sensors, and conduit types.

Figure 16:
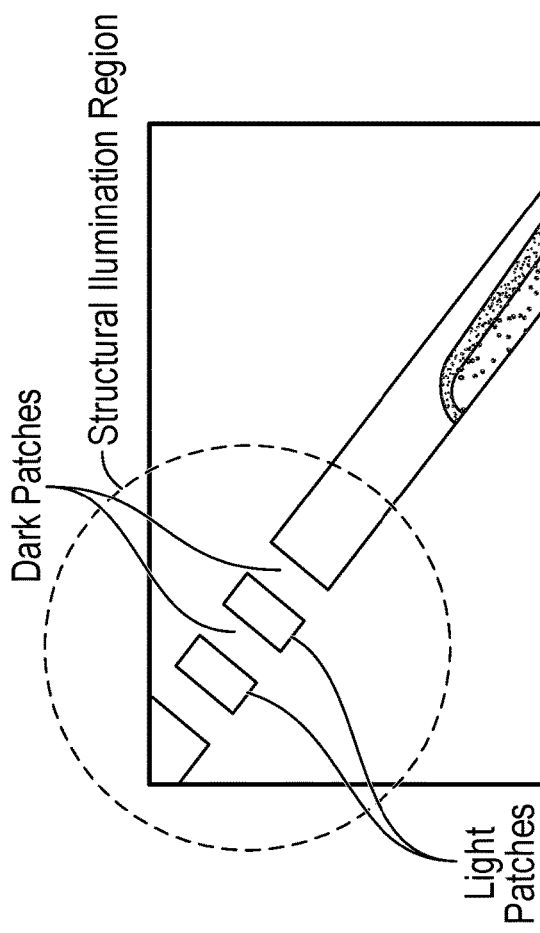
FIG. 16 is a diagram illustrating estimation of fluid component concentration based on particle scattering, according to some example embodiments.

FIG. 16 is a diagram illustrating estimation of fluid component concentration based on particle scattering, according to some example embodiments.

The system 100 may include a fluid scattering estimation module (e.g., within the sensor arrangement 110, the computing device 150, or any suitable combination thereof) that is or includes an algorithmic module configured to determine the presence of scattering particles, which may be performed as part of estimating hemoglobin concentration in blood at different hemolysis levels that cause variations in scattering parameters.

The fluid scattering estimation module utilizes a special heterogeneous illumination assembly to disambiguate the scattering and absorption parameters of the fluidic content.

In some variations, heterogeneous illumination is achieved by (i) placing LEDs or other light sources apart at some distance, (ii) using structured LEDs or other light sources, or (iii) creating a custom-structured light source by passing uniform light through a structured grating. Heterogeneous illumination may create brighter patches and darker patches when viewed by optical sensors. The fluid scattering estimation module analyzes the signal difference between the brighter patches and the darker patches to estimate the scattering parameter of the fluidic content (e.g., in combination with a computer vision algorithm or other machine learning algorithm, such as a deep learning algorithm).

In some variations, conduits of different types are used to create structural differences for the illumination.

The system 100 may include an optical mass calibration module (e.g., within the sensor arrangement 110, the computing device 150, or any suitable combination thereof) that is or includes an algorithmic module configured to translate the measurement from an optical sensor to the concentration or mass of the measured substance.

The measurement from the optical sensor (e.g., a video sensor) is in an arbitrary unit, and the resulting information is translated to obtain the distinct property of the fluidic content, such as the concentration of a fluid component of the fluidic content or the mass of the fluid component.

In some variations, the optical mass calibration module translates optical mass into the mass of the measured substance (e.g., the fluid component of interest, such as blood) by a trained mathematical model. A learning machine is trained with a mathematical model by calibrating the differential optical mass against any ground truth measurement (e.g., using a weighing scale). For each measured substance, the learning machine can be trained by one or multiple datasets with different concentration combinations.

In some variations, the optical mass calibration module translates optical mass into the concentration of the measured substance (e.g., the fluid component of interest) by a trained mathematical model. The mathematical model may be trained by machine learning (e.g., using a deep learning algorithm).

The system 100 may include a fluid type classification module (e.g., within the sensor arrangement 110, the computing device 150, or any suitable combination thereof) that is or includes an algorithmic module configured to classify the fluidic contents (e.g., determine a fluid type of the fluidic contents) within a given time frame.

The fluid type classification module automatically categorizes different fluidic content with different properties based on the output of the sensor arrangement or other measuring modality. The classification can be done at any given time frame with supplemental algorithmic logic.

In some variations, the fluid type classification module classifies laminar and non-laminar flow from an optical sensor.

Figure 17:
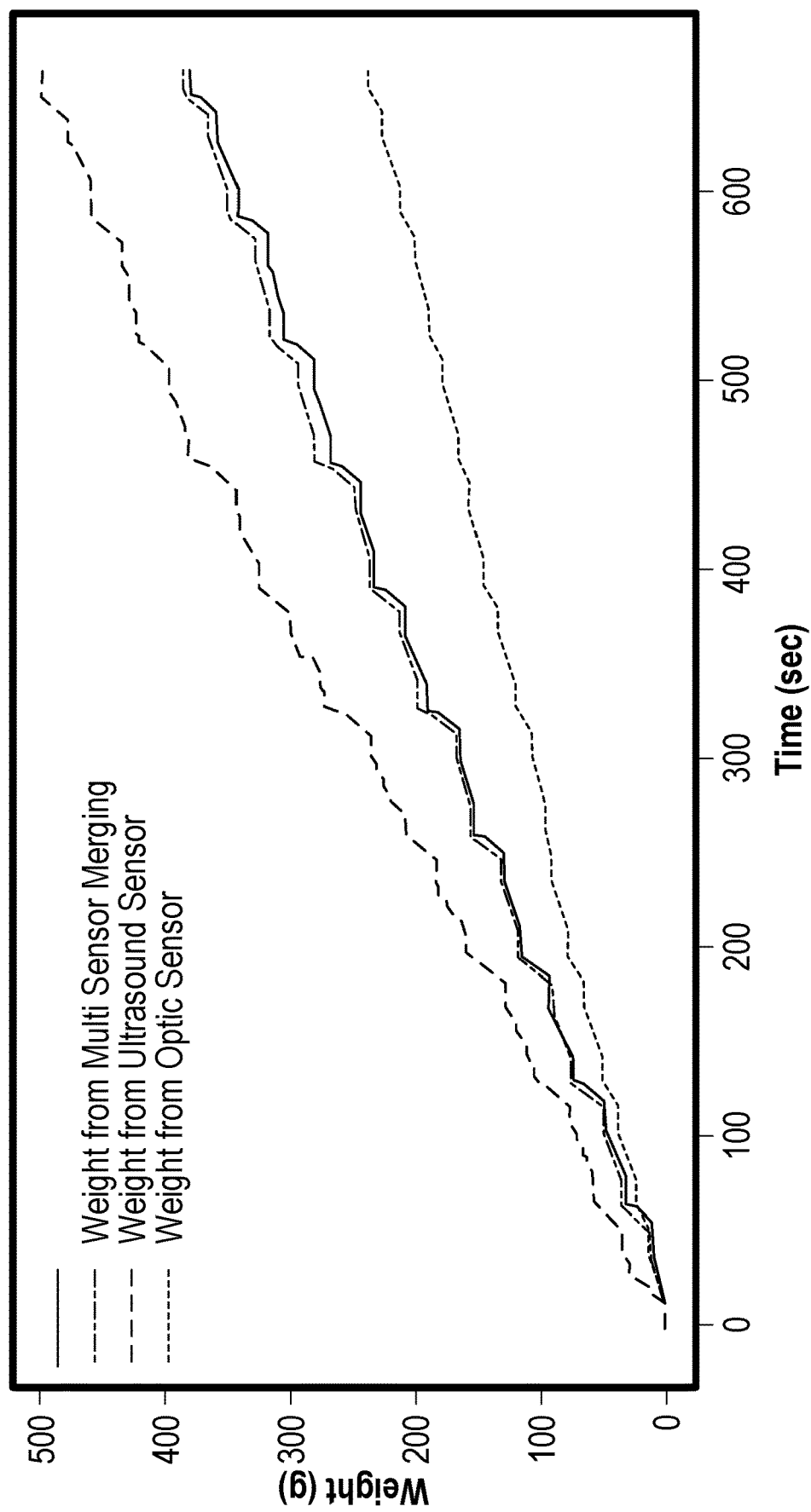
FIG. 17 is a graph illustrating a mathematical merge of results from various types of sensors, according to some example embodiments.

FIG. 17 is a graph illustrating a mathematical merge of results from various types of sensors, according to some example embodiments.

The system 100 may include a sensor merging module (e.g., within the sensor arrangement 110, the computing device 150, or any suitable combination thereof) that is or includes an algorithmic module configured to combine measurement of measured substance between different sensors (e.g., with different measuring modalities).

To maximize the advantages of different sensors with different properties, a mathematical merge function is used to appoint a weight of importance on different types of sensors. The mathematical merge function is derived from the properties and the condition of the fluidic content.

In some variations, the sensor merging module combines measurement between an ultrasound sensor and an optical sensor using a merge function derived from the fluid type classification module and the weight of accuracy on different sensors at different fluid conditions.

Any one or more of the components (e.g., modules) described herein may be implemented using hardware alone (e.g., one or more processors) or a combination of hardware and software. For example, any component described herein may physically include an arrangement of one or more processors configured to perform the operations described herein for that component. As another example, any component described herein may include software, hardware, or both, that configure an arrangement of one or more processors to perform the operations described herein for that component. Accordingly, different components described herein may include and configure different arrangements of processors at different points in time or a single arrangement of such processors at different points in time. Each component (e.g., module) described herein is an example of a means for performing the operations described herein for that component. Moreover, any two or more components described herein may be combined into a single component, and the functions described herein for a single component may be subdivided among multiple components. Furthermore, according to various example embodiments, components described herein as being implemented within a single system or machine (e.g., a single device) may be distributed across multiple systems or machines (e.g., multiple devices).

Any of the systems or machines (e.g., devices) discussed herein may be, include, or otherwise be implemented in a special-purpose (e.g., specialized or otherwise non-conventional and non-generic) computer that has been modified to perform one or more of the functions described herein for that system or machine (e.g., configured or programmed by special-purpose software, such as one or more software modules of a special-purpose application, operating system, firmware, middleware, or other software program). For example, a special-purpose computer system able to implement any one or more of the methodologies described herein is discussed below with respect to FIG. 18, and such a special-purpose computer may accordingly be a means for performing any one or more of the methodologies discussed herein. Within the technical field of such special-purpose computers, a special-purpose computer that has been specially modified (e.g., configured by special-purpose software) by the structures discussed herein to perform the functions discussed herein is technically improved compared to other special-purpose computers that lack the structures discussed herein or are otherwise unable to perform the functions discussed herein. Accordingly, a special-purpose machine configured according to the systems and methods discussed herein provides an improvement to the technology of similar special-purpose machines. Moreover, any two or more of the systems or machines discussed herein may be combined into a single system or machine, and the functions described herein for any single system or machine may be subdivided among multiple systems or machines.

Figure 18:
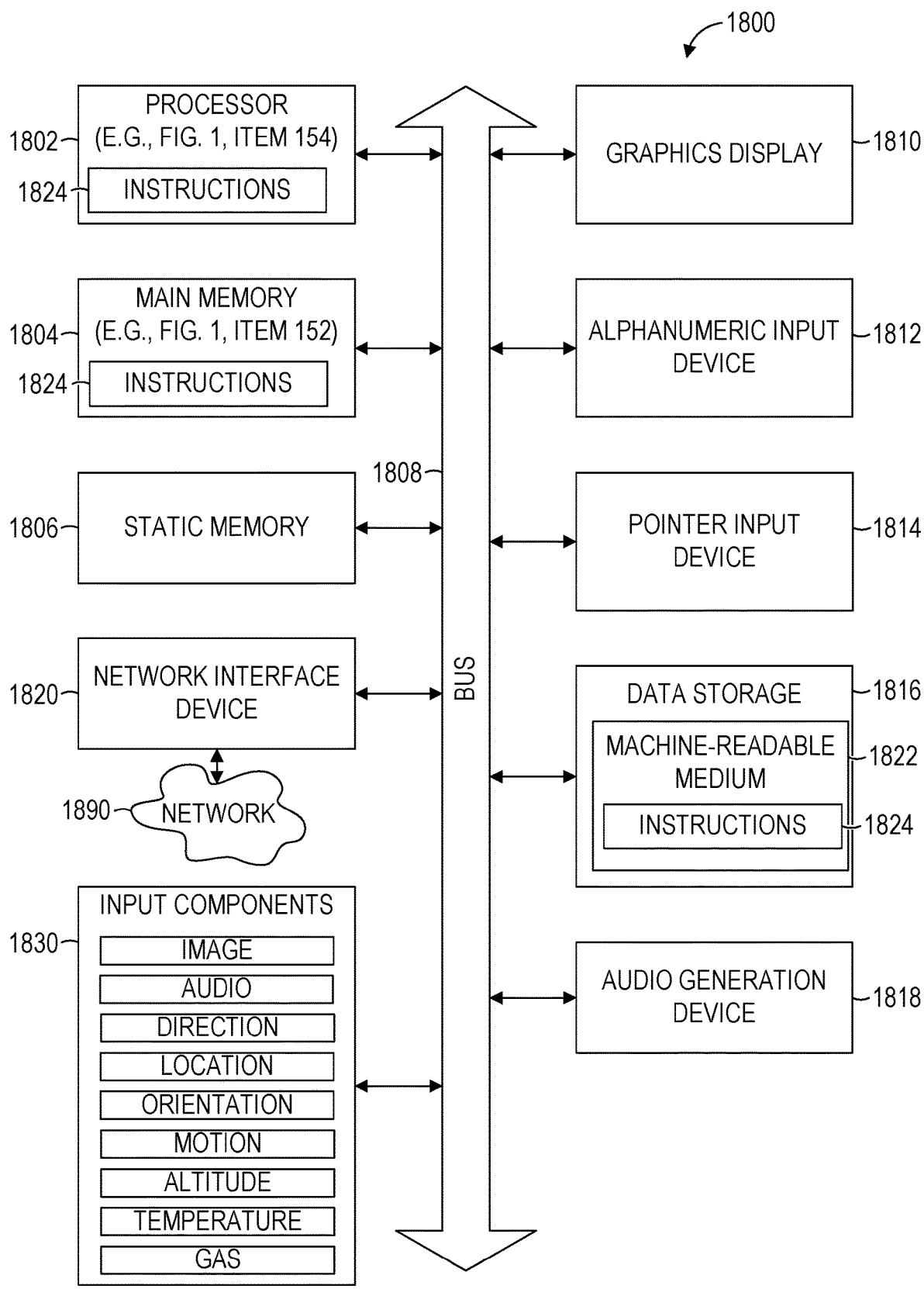
FIG. 18 is a block diagram illustrating components of a machine, according to some example embodiments, able to read instructions from a machine-readable medium and perform any one or more of the methodologies discussed herein.

FIG. 18 is a block diagram illustrating components of a machine 1800 (e.g., the computing device 150), according to some example embodiments, able to read instructions 1824 from a machine-readable medium 1822 (e.g., a non-transitory machine-readable medium, a machine-readable storage medium, a computer-readable storage medium, or any suitable combination thereof) and perform any one or more of the methodologies discussed herein, in whole or in part. Specifically, FIG. 18 shows the machine 1800 in the example form of a computer system (e.g., a computer) within which the instructions 1824 (e.g., software, a program, an application, an applet, an app, or other executable code) for causing the machine 1800 to perform any one or more of the methodologies discussed herein may be executed, in whole or in part.

In alternative embodiments, the machine 1800 operates as a standalone device or may be communicatively coupled (e.g., networked) to other machines. In a networked deployment, the machine 1800 may operate in the capacity of a server machine or a client machine in a server-client network environment, or as a peer machine in a distributed (e.g., peer-to-peer) network environment. The machine 1800 may be a server computer, a client computer, a personal computer (PC), a tablet computer, a laptop computer, a netbook, a cellular telephone, a smart phone, a set-top box (STB), a personal digital assistant (PDA), a web appliance, a network router, a network switch, a network bridge, or any machine capable of executing the instructions 1824, sequentially or otherwise, that specify actions to be taken by that machine. Further, while only a single machine is illustrated, the term "machine" shall also be taken to include any collection of machines that individually or jointly execute the instructions 1824 to perform all or part of any one or more of the methodologies discussed herein.

The machine 1800 includes a processor 1802 (e.g., one or more central processing units (CPUs), one or more graphics processing units (GPUs), one or more digital signal processors (DSPs), one or more application specific integrated circuits (ASICs), one or more radio-frequency integrated circuits (RFICs), or any suitable combination thereof), a main memory 1804, and a static memory 1806, which are configured to communicate with each other via a bus 1808. The processor 1802 contains solid-state digital microcircuits (e.g., electronic, optical, or both) that are configurable, temporarily or permanently, by some or all of the instructions 1824 such that the processor 1802 is configurable to perform any one or more of the methodologies described herein, in whole or in part. For example, a set of one or more microcircuits of the processor 1802 may be configurable to execute one or more modules (e.g., software modules) described herein. In some example embodiments, the processor 1802 is a multicore CPU (e.g., a dual-core CPU, a quad-core CPU, an 8-core CPU, or a 128-core CPU) within which each of multiple cores behaves as a separate processor that is able to perform any one or more of the methodologies discussed herein, in whole or in part. Although the beneficial effects described herein may be provided by the machine 1800 with at least the processor 1802, these same beneficial effects may be provided by a different kind of machine that contains no processors (e.g., a purely mechanical system, a purely hydraulic system, or a hybrid mechanical-hydraulic system), if such a processor-less machine is configured to perform one or more of the methodologies described herein.

The machine 1800 may further include a graphics display 1810 (e.g., a plasma display panel (PDP), a light emitting diode (LED) display, a liquid crystal display (LCD), a projector, a cathode ray tube (CRT), or any other display capable of displaying graphics or video). The machine 1800 may also include an alphanumeric input device 1812 (e.g., a keyboard or keypad), a pointer input device 1814 (e.g., a mouse, a touchpad, a touchscreen, a trackball, a joystick, a stylus, a motion sensor, an eye tracking device, a data glove, or other pointing instrument), a data storage 1316, an audio generation device 1318 (e.g., a sound card, an amplifier, a speaker, a headphone jack, or any suitable combination thereof), and a network interface device 1820.

The data storage 1316 (e.g., a data storage device) includes the machine-readable medium 1822 (e.g., a tangible and non-transitory machine-readable storage medium) on which are stored the instructions 1824 embodying any one or more of the methodologies or functions described herein. The instructions 1824 may also reside, completely or at least partially, within the main memory 1804, within the static memory 1806, within the processor 1802 (e.g., within the processor's cache memory), or any suitable combination thereof, before or during execution thereof by the machine 1800. Accordingly, the main memory 1804, the static memory 1806, and the processor 1802 may be considered machine-readable media (e.g., tangible and non-transitory machine-readable media). The instructions 1824 may be transmitted or received over a network 1890 via the network interface device 1820. For example, the network interface device 1820 may communicate the instructions 1824 using any one or more transfer protocols (e.g., hypertext transfer protocol (HTTP)).

In some example embodiments, the machine 1800 may be a portable computing device (e.g., a smart phone, a tablet computer, or a wearable device), and may have one or more additional input components 1830 (e.g., sensors or gauges). Examples of such input components 1830 include an image input component (e.g., one or more cameras), an audio input component (e.g., one or more microphones), a direction input component (e.g., a compass), a location input component (e.g., a global positioning system (GPS) receiver), an orientation component (e.g., a gyroscope), a motion detection component (e.g., one or more accelerometers), an altitude detection component (e.g., an altimeter), a temperature input component (e.g., a thermometer), and a gas detection component (e.g., a gas sensor). Input data gathered by any one or more of these input components 1830 may be accessible and available for use by any of the modules described herein (e.g., with suitable privacy notifications and protections, such as opt-in consent or opt-out consent, implemented in accordance with user preference, applicable regulations, or any suitable combination thereof).

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 1822 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of carrying (e.g., storing or communicating) the instructions 1824 for execution by the machine 1800, such that the instructions 1824, when executed by one or more processors of the machine 1800 (e.g., processor 1802), cause the machine 1800 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible and non-transitory data repositories (e.g., data volumes) in the example form of a solid-state memory chip, an optical disc, a magnetic disc, or any suitable combination thereof.

A "non-transitory" machine-readable medium, as used herein, specifically excludes propagating signals per se. According to various example embodiments, the instructions 1824 for execution by the machine 1800 can be communicated via a carrier medium (e.g., a machine-readable carrier medium). Examples of such a carrier medium include a non-transient carrier medium (e.g., a non-transitory machine-readable storage medium, such as a solid-state memory that is physically movable from one place to another place) and a transient carrier medium (e.g., a carrier wave or other propagating signal that communicates the instructions 1824).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module in which the hardware includes one or more processors. Accordingly, the operations described herein may be at least partially processor-implemented, hardware-implemented, or both, since a processor is an example of hardware, and at least some operations within any one or more of the methods discussed herein may be performed by one or more processor-implemented modules, hardware-implemented modules, or any suitable combination thereof.

Moreover, such one or more processors may perform operations in a "cloud computing" environment or as a service (e.g., within a "software as a service" (SaaS) implementation). For example, at least some operations within any one or more of the methods discussed herein may be performed by a group of computers (e.g., as examples of machines that include processors), with these operations being accessible via a network (e.g., the Internet) and via one or more appropriate interfaces (e.g., an application program interface (API)). The performance of certain operations may be distributed among the one or more processors, whether residing only within a single machine or deployed across a number of machines. In some example embodiments, the one or more processors or hardware modules (e.g., processor-implemented modules) may be located in a single geographic location (e.g., within a home environment, an office environment, or a server farm). In other example embodiments, the one or more processors or hardware modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and their functionality presented as separate components and functions in example configurations may be implemented as a combined structure or component with combined functions. Similarly, structures and functionality presented as a single component may be implemented as separate components and functions. These and other variations, modifications, additions, and improvements fall within the scope of the subject matter herein.

Some portions of the subject matter discussed herein may be presented in terms of algorithms or symbolic representations of operations on data stored as bits or binary digital signals within a memory (e.g., a computer memory or other machine memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "accessing," "processing," "detecting," "computing," "calculating," "determining," "generating," "presenting," "displaying," or the like refer to actions or processes performable by a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The following enumerated descriptions describe various examples of methods, machine-readable media, and systems (e.g., machines, devices, or other apparatus) discussed herein.

A first example provides a method for characterizing patient fluid loss by a patient, the method comprising:
  quantifying flow of fluidic content through a conduit, the fluidic content comprising a patient fluid;
  estimating a concentration of a fluid component in the patient fluid; and
  characterizing patient fluid loss based at least in part on the quantified flow and the concentration of the fluid component,
  wherein at least one of the flow rate and the concentration of the fluid component is based on sampling data from a sensor arrangement coupled to the conduit.

A second example provides a method according to the first example, wherein the patient fluid is blood, and the fluid component is hemoglobin.

A third example provides a method according to the first example or the second example, wherein characterizing patient fluid loss comprises quantifying volume of blood flowing through the conduit.

A fourth example provides a method according to any of the first through third examples, further comprising measuring composition of the fluidic content.

A fifth example provides a method according to the fourth example, wherein measuring composition of the fluidic content comprises performing spectroscopic analysis.

A sixth example provides a method according to any of the first through fifth examples, wherein quantifying flow of fluidic content comprises estimating a flow rate of the fluidic content.

A seventh example provides a method according to the sixth example, wherein estimating the flow rate comprises emitting ultrasonic waves into the conduit and analyzing a frequency shift of ultrasonic waves reflected from the fluidic content.

An eighth example provides a method according to the sixth example, wherein estimating the flow rate comprises emitting ultrasonic waves into the conduit and analyzing time of flight of ultrasonic waves transmitted through the fluidic content.

A ninth example provides a method according to the sixth example, wherein estimating the flow rate comprises comparing a first optical signal and a second optical signal, the first optical signal corresponding to light detected at a first location along the conduit and the second optical signal corresponding to light detected at a second location along the conduit.

A tenth example provides a method according to any of the first through ninth examples, wherein quantifying flow of fluidic content comprises estimating a thermal mass flow of the fluidic content.

An eleventh example provides a method according to any of the first through tenth examples, wherein estimating the concentration of a fluid component comprises analyzing a multispectral image of the conduit.

A twelfth example provides a method according to any of the first through eleventh examples, further comprising reducing the flow of the fluidic content through the conduit while quantifying the flow of the fluidic content.

A thirteenth example provides a system for characterizing patient fluid loss by a patient, the system comprising:
- a sensor arrangement couplable to a conduit, the sensor arrangement comprising:
  - at least one sensor configured to quantify flow of fluidic content through the conduit, the fluidic content comprising a patient fluid, and to estimate a concentration of a fluid component in the patient fluid.

A fourteenth example provides a system according to the thirteenth example, wherein the sensor arrangement comprises a housing configured to cover at least a portion of the conduit.

A fifteenth example provides a system according to the thirteenth example or the fourteenth example, wherein the housing comprises jaws configured to clamp onto the conduit.

A sixteenth example provides a system according to any of the thirteenth through fifteenth examples, further comprising a conduit insert couplable inline with the conduit.

A seventeenth example provides a system according to any of the thirteenth through sixteenth examples, wherein the at least one sensor comprises an ultrasound flow rate sensor.

An eighteenth example provides a system according to any of the thirteenth through seventeenth examples, wherein the at least one sensor comprises an optical sensor configured to detect light transmitted through the fluidic content.

A nineteenth example provides a system according to any of the thirteenth through eighteenth examples, wherein the sensor arrangement comprises a plurality of optical sensors arranged at a plurality of axial locations along the conduit.

A twentieth example provides a system according to any of the thirteenth through nineteenth examples, wherein the sensor arrangement comprises a plurality of optical sensors arranged at a plurality of circumferential locations around the conduit.

A twenty-first example provides a system according to any of the thirteenth through twentieth examples, wherein the sensor arrangement comprises a plurality of optical sensors arranged helically around the conduit.

A twenty-second example provides a system according to any of the thirteenth through twenty-first examples, wherein the at least one sensor comprises a thermal mass flow sensor.

A twenty-third example provides a system according to any of the thirteenth through twenty-second examples, wherein the at least one sensor comprises an optical sensor array configured to perform multispectral imaging.

A twenty-fourth example provides a system according to any of the thirteenth through twenty-third examples, wherein the at least one sensor comprises an optical sensor array configured to perform color imaging.

A twenty-fifth example provides a system according to any of the thirteenth through twenty-fourth examples, further comprising a processor configured to characterize patient fluid loss based at least in part on the quantified flow and the concentration of the fluid component.

A twenty-sixth example provides a carrier medium carrying machine-readable instructions for controlling a machine to carry out the operations (e.g., method operations) performed in any one of the previously described examples.

What is claimed is:

1. A method comprising:
   accessing sensor data from a sensor arrangement included in a housing configured to position the sensor arrangement proximate to and covering at least a portion of a conduit through which fluidic content is flowing, the fluidic content including a patient fluid, the flow of the fluidic content through the conduit includes a first region of continuous flow and a second region of non-continuous flow, and the sensor data including a first output from an ultrasound sensor based on the first region of continuous flow and a second output from an optical sensor based on the second region of non-continuous flow;
   estimating a volumetric flow rate of the fluidic content flowing through the conduit;
   estimating a concentration of a fluid component of the patient fluid in the fluidic content flowing through the conduit; and
   by one or more processors, characterizing passage of the patient fluid through the conduit based on the estimated volumetric flow rate of the fluidic content and on the estimated concentration of the fluid component in the fluidic content, at least one of the estimating of the volumetric flow rate or the estimating of the concentration being based on the sensor data from the sensor arrangement positioned proximate to the conduit by the housing,
   wherein estimating of the volumetric flow rate of the fluidic content is based on the first output from the ultrasound sensor and the second output from the optical sensor and includes emitting outgoing ultrasonic waves into the conduit and determining at least one of: a frequency shift of incoming ultrasonic waves reflected from the fluidic content, and a time of flight of ultrasonic waves transmitted through the fluidic content.

2. The method of claim 1, wherein the patient fluid is blood, and the fluid component is hemoglobin.

3. The method of claim 1, wherein the characterizing of the passage of the patient fluid includes quantifying a volume of blood flowing through the conduit.

4. The method of claim 1, wherein the estimating of the concentration of the fluid component in the fluidic content flowing through the conduit includes measuring a composition of the fluidic content.

5. The method of claim 4, wherein the measuring of the composition of the fluidic content includes performing a spectroscopic analysis of the fluidic content flowing through the conduit.

6. The method of claim 1, wherein the estimating of the volumetric flow rate of the fluidic content further includes comparing a first optical signal to a second optical signal, the first optical signal indicating light detected at a first location along the conduit, the second optical signal indicating light detected at a second location along the conduit.

7. The method of claim 1, wherein estimating the volumetric flow rate of the fluidic content further includes estimating a mass flow rate of the fluidic content.

8. The method of claim 1, wherein the estimating of the concentration of the fluid component in the fluidic content is based on a multispectral image of the conduit in which the fluidic content is flowing.

9. The method of claim 1, further comprising reducing the flow of the fluidic content through the conduit; and wherein estimating the volumetric flow rate of the fluidic content includes estimating a reduced flow of the fluidic content.

10. The method of claim 1, wherein:
estimating the volumetric flow rate of the fluidic content includes inputting the sensor data into a learning machine trained to quantify candidate flows based on a training set of reference flows represented by reference sensor data, the trained learning machine outputting the estimated volumetric flow rate of the fluidic content based on the inputted sensor data.

11. A method comprising:
accessing sensor data from a sensor arrangement included in a housing configured to position the sensor arrangement proximate to and covering at least a portion of a conduit through which fluidic content is flowing, the fluidic content including a patient fluid;
estimating a volumetric flow rate of the fluidic content flowing through the conduit;
estimating a concentration of a fluid component of the patient fluid in the fluidic content flowing through the conduit; and
by one or more processors, characterizing passage of the patient fluid through the conduit based on the estimated volumetric flow rate of the fluidic content and on the estimated concentration of the fluid component in the fluidic content, at least one of the estimating of the volumetric flow rate or the estimating of the concentration being based on the sensor data from the sensor arrangement positioned proximate to the conduit by the housing,
wherein estimating the volumetric flow rate of the fluidic content includes comparing a first optical signal to a second optical signal, the first optical signal indicating light detected at a first location along the conduit, and the second optical signal indicating light detected at a second location along the conduit.

12. The method of claim 11, wherein the first and second optical signals are digital signals generated by first and second optical sensors included in the sensor arrangement.

13. The method of claim 11, wherein the first and second locations are axially spaced along the conduit.

14. The method of claim 11, wherein the first and second locations are circumferentially spaced around the conduit.

15. The method of claim 11, wherein the first and second locations are helically arranged about the conduit.

16. The method of claim 11, further comprising estimating a mass flow rate of the fluidic content with a thermal mass flow sensor.

17. The method of claim 11, further comprising performing multispectral imaging of the fluidic content with the first and second optical sensors.

18. The method of claim 11, further comprising performing color imaging of the fluidic content with the first and second optical sensors.

19. The method of claim 11, wherein estimating of the volumetric flow rate of the fluidic content further includes emitting outgoing ultrasonic waves into the conduit and determining at least one of: a frequency shift of incoming ultrasonic waves reflected from the fluidic content, and a time of flight of ultrasonic waves transmitted through the fluidic content.

20. The method of claim 19, wherein:
the flow of the fluidic content through the conduit includes a first region of continuous flow and a second region of non-continuous flow;
the sensor data further includes a first output from an ultrasound sensor based on the first region of continuous flow and a second output from an optical sensor based on the second region of non-continuous flow; and
estimating the volumetric flow rate of the fluidic content includes estimating a flow rate based on the first output from the ultrasound sensor and based on the second output from the optical sensor.

21. The method of claim 11, further comprising:
estimating the volumetric flow rate of the fluidic content includes inputting the sensor data into a learning machine trained to quantify candidate flows based on a training set of reference flows represented by reference sensor data, the trained learning machine outputting the estimated volumetric flow rate of the fluidic content based on the inputted sensor data.

* * * * *